United States Patent
Barrios Sierra et al.

(10) Patent No.: US 12,383,639 B2
(45) Date of Patent: Aug. 12, 2025

(54) DIRECTIONAL ULTRAVIOLET PROJECTION DEVICES AND RELATED METHODS OF USE

(71) Applicant: Anram Holdings, Mississauga (CA)

(72) Inventors: Jose Miguel Barrios Sierra, Toronto (CA); Prashant Vijayrao Mane, Oakville (CA); Romil Hitenbhai Dalvadi, Brampton (CA); Bhavana Alangekar, Mississauga (CA)

(73) Assignee: Anram Holdings, Oakville (CA)

( * ) Notice: Subject to any disclaimer, the term of this patent is extended or adjusted under 35 U.S.C. 154(b) by 918 days.

(21) Appl. No.: 17/319,166

(22) Filed: May 13, 2021

(65) Prior Publication Data
US 2022/0152237 A1    May 19, 2022

Related U.S. Application Data

(60) Provisional application No. 63/115,454, filed on Nov. 18, 2020.

(51) Int. Cl.
*A61L 2/10*    (2006.01)

(52) U.S. Cl.
CPC ............. *A61L 2/10* (2013.01); *A61L 2202/11* (2013.01); *A61L 2202/16* (2013.01)

(58) Field of Classification Search
CPC .... A61L 2/10; A61L 2202/11; A61L 2202/16; A61L 9/20; A61L 2202/14; A61L 2202/25
See application file for complete search history.

(56) References Cited

U.S. PATENT DOCUMENTS

| | | |
|---|---|---|
| 9,603,956 B2 | 3/2017 | Newham |
| 10,583,212 B2 | 3/2020 | Ufkes |
| 10,639,390 B2 * | 5/2020 | Lloyd .................... A61L 2/10 |
| 2018/0256764 A1 | 9/2018 | Kreitenberg |

(Continued)

FOREIGN PATENT DOCUMENTS

| | | |
|---|---|---|
| AU | 2017356855 | 5/2019 |
| CA | 3087876 | 8/2019 |
| EP | 2496271 | 9/2012 |

(Continued)

OTHER PUBLICATIONS

Dimer Leaders in UVC Innovation Since 2012; Introducing the UVHammer; retrieved https://www.dimeruv.com/; 2020.

(Continued)

*Primary Examiner* — Sean E Conley
*Assistant Examiner* — Brendan A Hensel
(74) *Attorney, Agent, or Firm* — Rowand LLP

(57) ABSTRACT

Embodiments of the present disclosure provide an apparatus and a method for projecting UV light towards surfaces across a path. The apparatus includes a mobile body and including opposing lateral sides and a sagittal plane passing between them. The apparatus also includes a projection head rotatably mounted to the mobile body. The projection head operates to project UV light directionally towards surfaces located above and proximate to the opposing lateral sides, where the projection head is adapted to rotate about a horizontal axis in the sagittal plane while the UV light is being projected towards the surfaces.

19 Claims, 14 Drawing Sheets

(56) References Cited

U.S. PATENT DOCUMENTS

2020/0078480 A1   3/2020  Starkweather et al.
2020/0268915 A1*  8/2020  Kreitenberg ............... A61L 2/10

FOREIGN PATENT DOCUMENTS

KR      20150012971       2/2015
KR       101509616        3/2015
WO    WO-2018089288 A1 *  5/2018  ............... A61L 2/10

OTHER PUBLICATIONS

EPO, Extended European Search Report, relating to EP application No. 21172429.9, dated Nov. 4, 2021.
PCT International Searching Authority, International Search Report and Written Opinion relating to application No. PCT/CA2021/050661 dated Aug. 2, 2021.

* cited by examiner

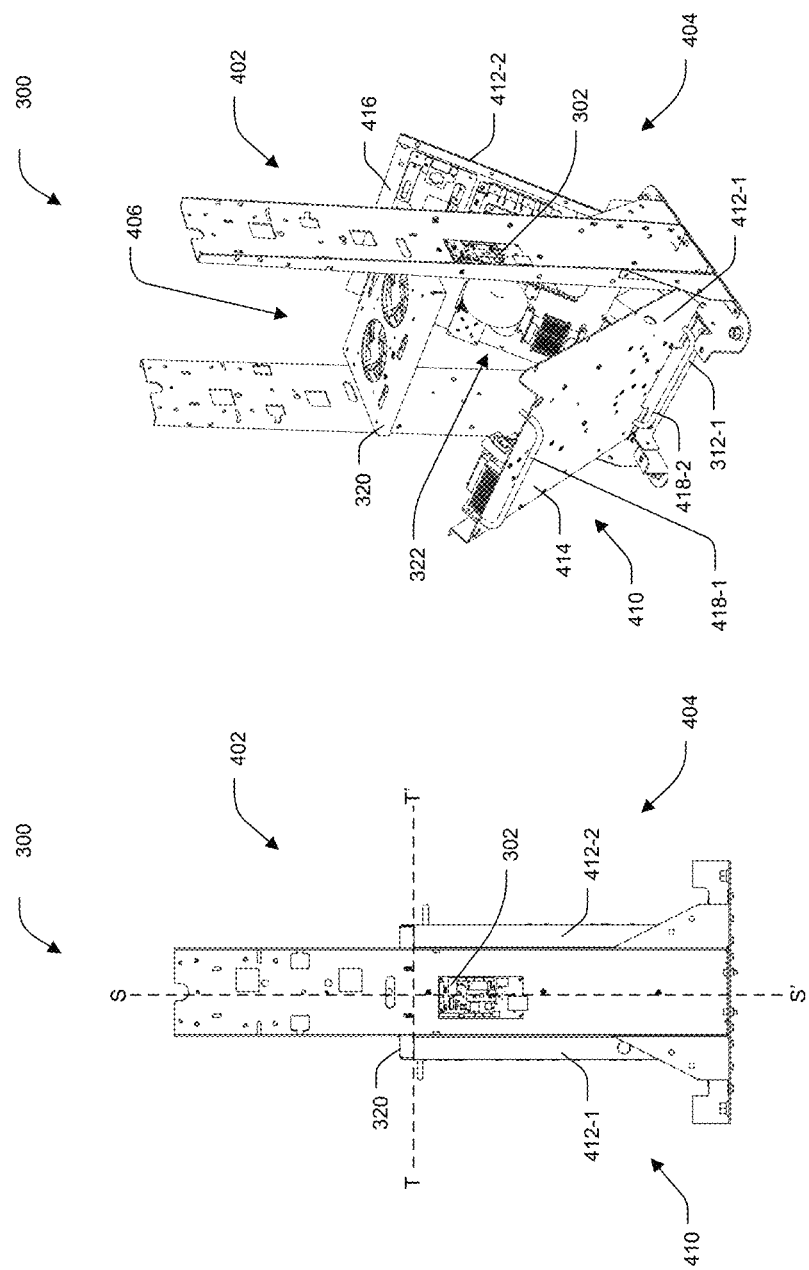

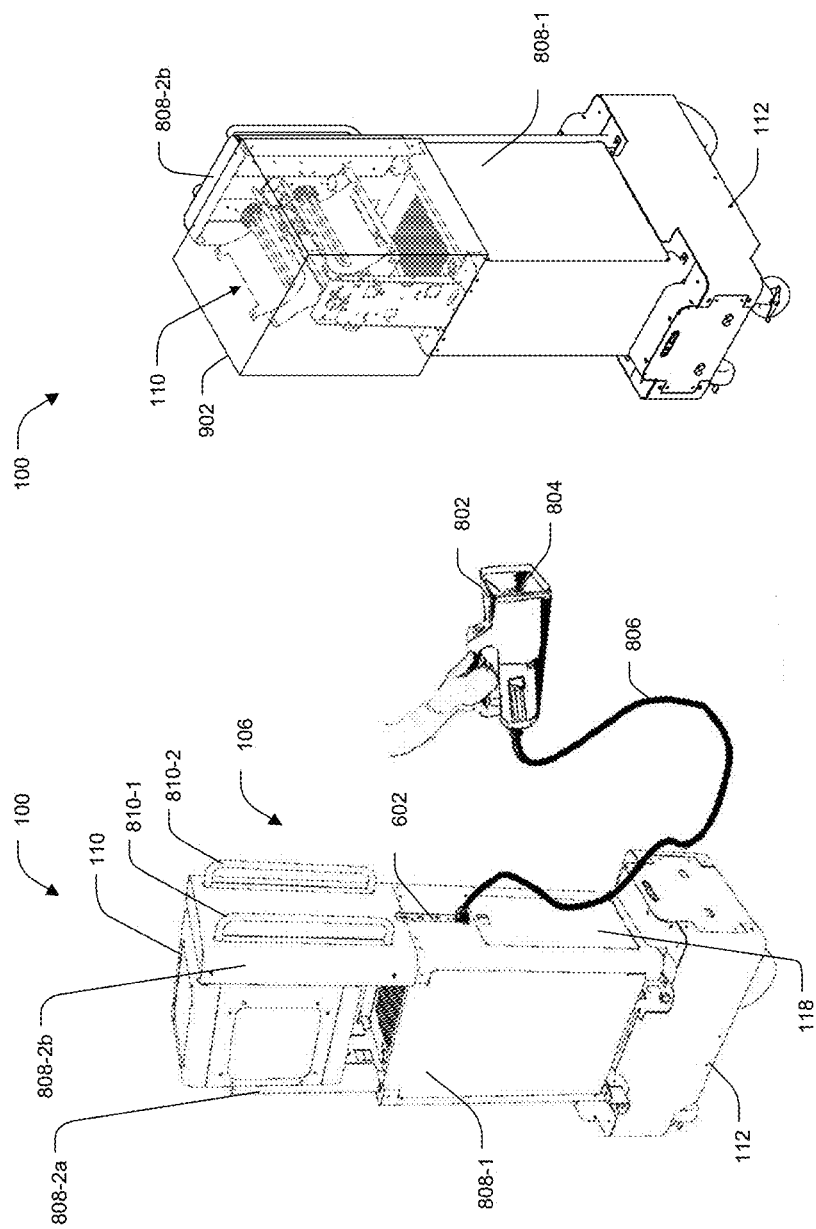

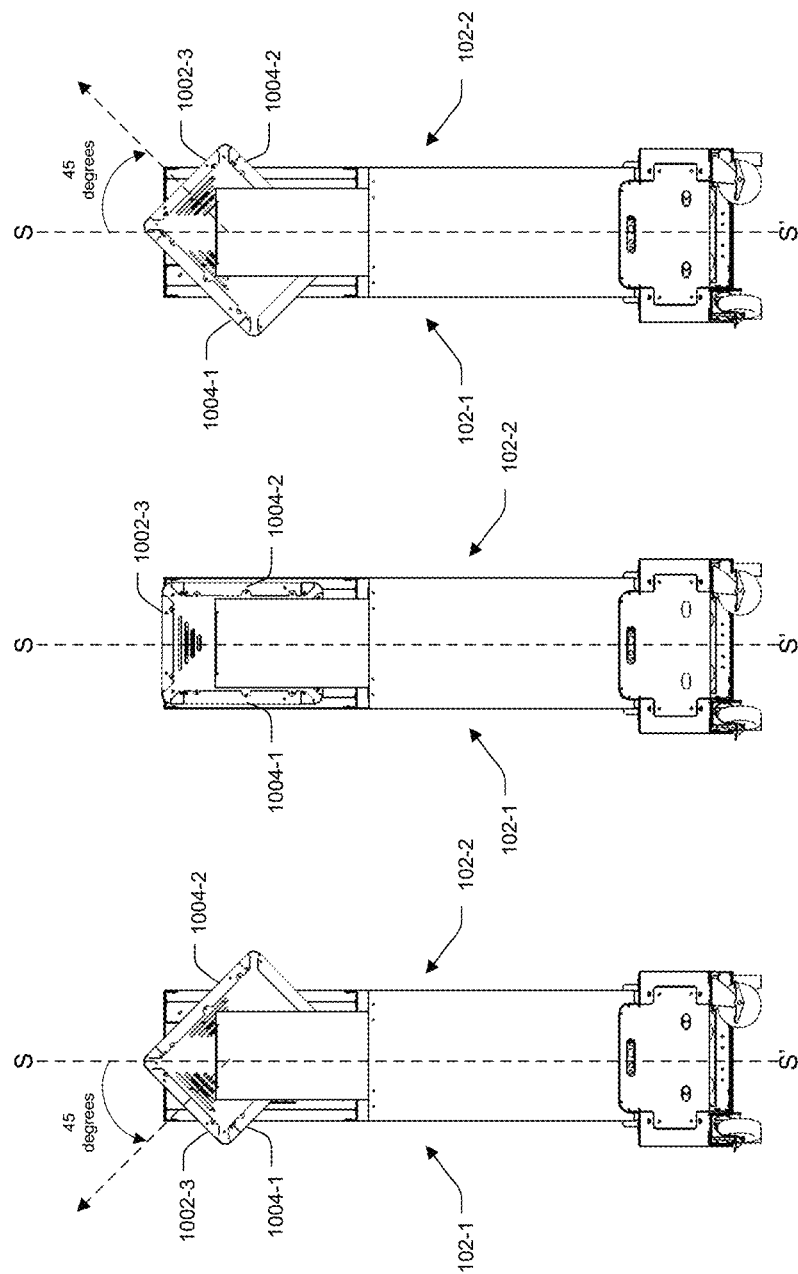

DIRECTIONAL ULTRAVIOLET PROJECTION DEVICES AND RELATED METHODS OF USE

TECHNICAL FIELD

The present disclosure generally relates to disinfection devices and particularly relates to directional ultraviolet projection devices and related methods of use.

BACKGROUND

Rapid surface disinfection is cardinal to a safe and productive work environment. Modern disinfection devices often include a source of ultraviolet (UV) light for surface disinfection. These devices typically project UV light in a single direction at any given instant to limit surface coverage and disinfection per unit time, or randomly project UV light in all directions to heighten energy wastage for disinfecting surfaces in a specific direction or plane.

SUMMARY

A traditional approach for directional disinfection of surfaces, e.g., across a path, includes a device mounted with one or more arms (or wings) fitted with UV lamps. The arms typically extend linearly or rotatably out of the device to deploy the UV lamps near the surfaces during operation. Such increase in arm geometry to set up the device for operation amplifies the total time required for sanitizing an area, operational costs, and area downtime. Moreover, each arm generally couples to a separate moving assembly for extension and orients the UV lamps to project UV light only towards surfaces on a single side of the device. Hence, such a conventional device relies on implementing multiple arms (or otherwise, compromise surface coverage) to increase the device manufacturing time and costs.

One embodiment of the present disclosure includes an apparatus for projecting UV light towards surfaces across a path. The apparatus includes a mobile body including opposing lateral sides and a sagittal plane passing between them. The apparatus also includes a projection head rotatably mounted to the mobile body. The projection head may operate to project UV light directionally towards surfaces located above and proximate to the opposing lateral sides, where the projection head is adapted to rotate about a horizontal axis in the sagittal plane while the UV light is being projected towards the surfaces.

Another embodiment of the present disclosure includes a method of projecting UV light towards surfaces across a path. The method includes providing a projection head including a mobile body having opposing lateral sides and a sagittal plane passing between them; projecting UV light from the projection head directionally towards surfaces located above and proximate to the opposing lateral sides; and rotating the projection head about a horizontal axis in the sagittal plane while the UV light is being projected towards the surfaces.

The above summary of exemplary embodiments is not intended to describe each disclosed embodiment or every implementation of the present disclosure. Other and further aspects and features of the disclosure would be evident from reading the following detailed description of the embodiments, which are intended to illustrate, not limit, the present disclosure.

BRIEF DESCRIPTION OF THE DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein.

FIG. 4 is a front elevation view of the uniframe of FIG. 3 including an exemplary tray assembly in a closed position, according to an embodiment of the present disclosure.

FIG. 5 is a front perspective view of the uniframe of FIG. 3 including the tray assembly of FIG. 4 in an open position, according to an embodiment of the present disclosure.

FIG. 8 is a rear perspective view of the projection device of FIG. 1A coupled to an exemplary handheld device, according to an embodiment of the present disclosure.

FIG. 9 is a front perspective view of the projection device of FIG. 1A including an exemplary optically permeable housing, according to another embodiment of the present disclosure.

FIGS. 17A-17C illustrate an exemplary operation of the projection head of FIG. 10 for implementing the projection device of FIG. 1A, according to an embodiment of the present disclosure.

DETAILED DESCRIPTION

Figure 1:
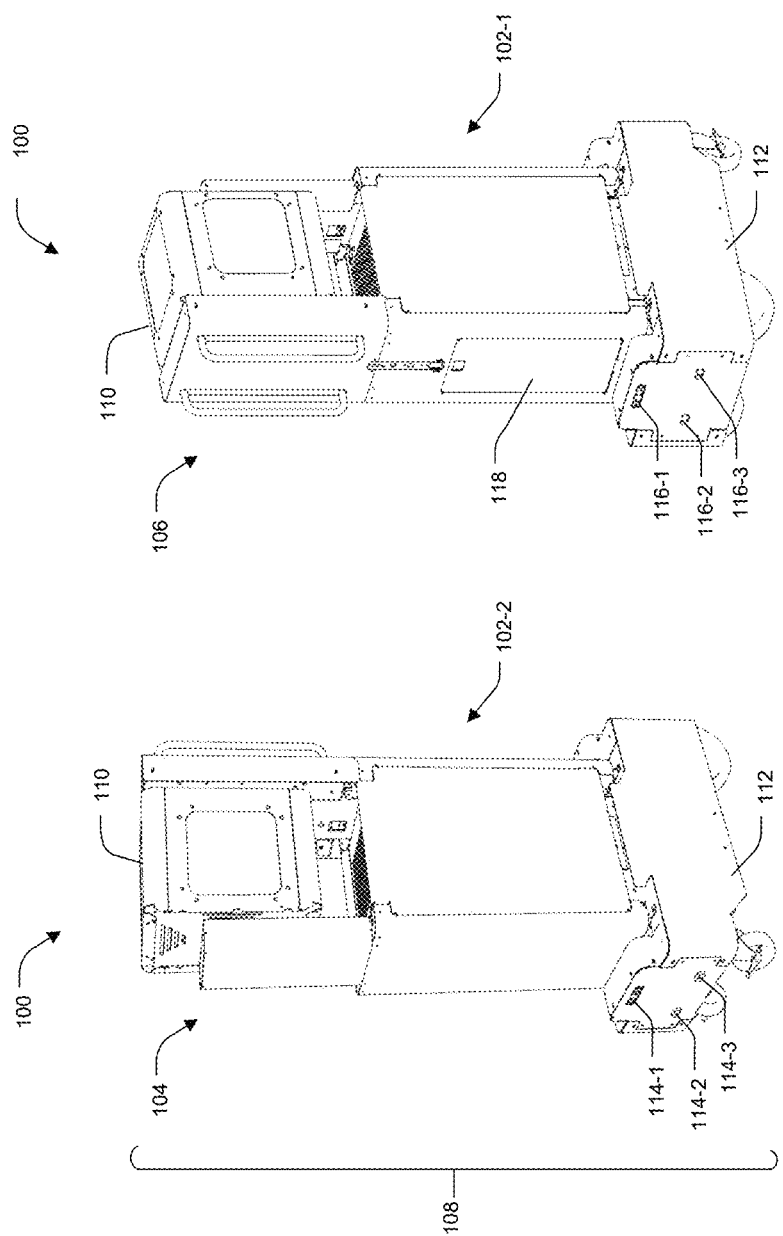
FIG. 1A is a front perspective view of an exemplary directional UV projection device (or projection device), according to an embodiment of the present disclosure.
FIG. 1B is a rear perspective view of the projection device of FIG. 1A, according to an embodiment of the present disclosure.
Figure 2:
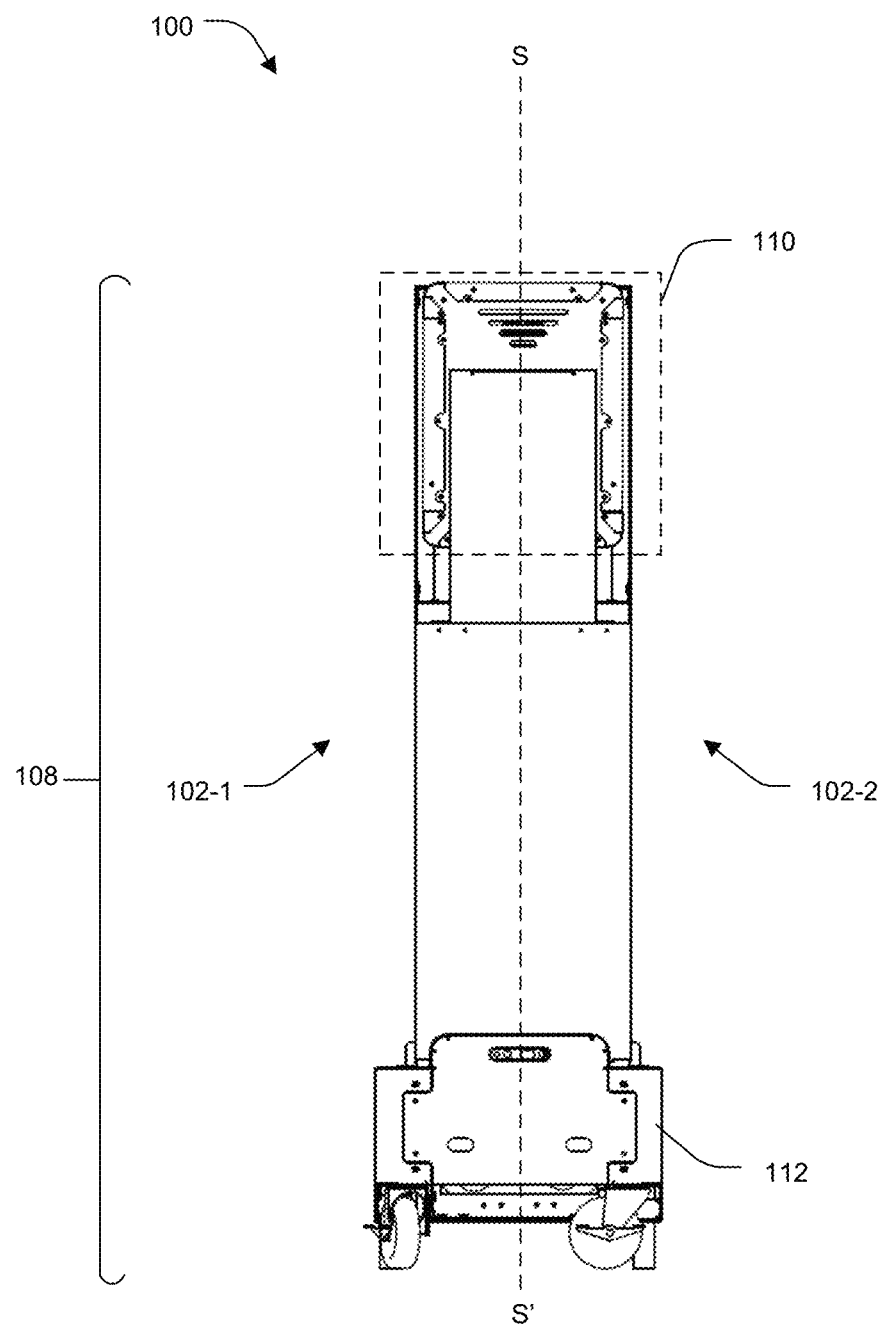
FIG. 2 is a front elevation view of the projection device of FIG. 1A, according to an embodiment of the present disclosure.

The following detailed description is provided with reference to the drawings herein. Exemplary embodiments are provided as illustrative examples so as to enable those skilled in the art to practice the disclosure. It will be appreciated that further variations of the concepts and embodiments disclosed herein can be contemplated. The examples of the present disclosure described herein may be used together in different combinations. In the following description, details are set forth in order to provide an understanding of the present disclosure. It will be readily apparent, however, that the present disclosure may be practiced without limitation to all these details. Also, throughout the present disclosure, the terms "a" and "an" are intended to denote at least one of a particular element. The terms "a" and "an" may also denote more than one of a particular element. As used herein, the term "includes" means includes but not limited to, the term "including" means including but not limited to. The term "based on" means based at least in part on, the term "based upon" means based at least in part upon, and the term "such as" means such as but not limited to. The term "approximately" means a variation of +/−5% in a stated number or a value of a stated parameter. Further, in the present disclosure, an embodiment showing a singular component should not be considered limiting; rather, the present disclosure is intended to encompass other embodiments including a plurality of the same or similar component, and vice-versa, unless explicitly stated otherwise herein. The present disclosure also encompasses present and future known equivalents of the components referred to herein.

Non-Limiting Definitions

Definitions of one or more terms that will be used in this disclosure are described below without limitations. For a person skilled in the art, it is understood that the definitions are provided only for the sake of clarity and are intended to include more examples than just provided below.

A term "software product" is used in the present disclosure in the context of its broadest definition. The software product may refer to a computer code implemented on a computer readable medium and operable to control or influence an intended function or task.

A term "software patch" is used in the present disclosure in the context of its broadest definition. The "software patch" may refer to a computer code designed to operate in combination with the software product. In some examples, the software patch may be an incomplete version of the software product.

A term "path" is used in the present disclosure in the context of its broadest definition. The path may refer to a passage between opposing surfaces. In one example, at least one of the opposing surfaces includes a portion of the ground. In another example, one of the opposing surfaces includes an elevated surface relative to the other. Other examples may include one of the opposing surfaces being positioned or oriented at a non-zero angle relative to a horizontal axis.

A term "sagittal plane" is used in the present disclosure in the context of its broadest definition. The sagittal plane may refer to an imaginary plane extending from a rear to a front of a component or device. The sagittal plane may divide such component or device into left and right parts. The sagittal plane may pass through a center of the component or device to split it into two halves; however, other examples may include the sagittal plane being off centered to split the component or device into unequal left and right parts.

A term "operational cycle" is used in the present disclosure in the context of its broadest definition. The operational cycle may refer to a period during which a device or component may be active for performing an intended task/operation. In some examples, the operational cycle may be predefined or dynamically defined based on clock times, a type of task (e.g., disinfection, communication, navigation, etc.), and a type of location (e.g., aircraft, room, auditorium, etc.) where such device or component may be intended for use.

Exemplary Embodiments

FIGS. 1A-1B are perspective views of an exemplary directional UV projection device, according to an embodiment of the present disclosure. The directional UV projection device 100 (hereinafter referred to as projection device 100) may be configured for a projection of a germicide directionally towards surfaces in planes above and lateral thereto. The germicide may include UV light alone or in combination with any other suitable types of energies or complementing agents. Examples of such energies may include, but are not limited to, radio, microwave, x-ray, infrared, visible, or any other specific wavelength or group of wavelengths in the electromagnetic spectrum. On the other hand, examples of such complementing agents may include, but are not limited to, chemical agents (e.g., alcohols, aldehydes, oxidizing agents, naturally occurring or modified compounds, etc.), physical agents (e.g., heat, pressure, vibration, sound, radiation, plasma, electricity, etc.), and biological agents (e.g., living organisms, plants or plant products, assistive-pathogens, organic residues, etc.) for catalyzing or effecting disinfection. In some instances, a type of energy or agent for use with the UV light may be selected based on an intended effect or an intended operation linked to a component of the projection device 100. Further, the projection device 100 may be operable to communicate with a computing device (not shown) over a wired or wireless network. Examples of such computing device may include, but are not limited to, a desktop computer, a personal digital assistant (PDA), a server, a mainframe computer, a mobile computing device (e.g., mobile phones, laptops, tablets, etc.), an internet appliance (e.g., a modem, a wireless access point, a router, a base station, a gateway, etc.), and so on.

The projection device 100 may be implemented as a standalone and/or dedicated mobile or portable device including hardware and installed software, where the hardware is closely matched to the requirements and/or functionality of the software for enabling localized as well as remote operations. In one embodiment, the projection device 100 may be implemented to, at least one of, (1) directionally project the germicide such as UV light towards surfaces above and lateral thereto, (2) limit or prevent dispersion of the germicide towards rear and front sides for better energy management while enabling targeted disinfection of surfaces, (3) have a compact geometry and footprint for traversing a narrow path such as an aircraft aisle and minimizing deployment time, (4) move autonomously while directionally projecting the germicide towards these surfaces, (5) selectively rotate or tilt germicide sources while directionally projecting the germicide towards the surfaces, (6) project the germicide in either pulsed and/or continuous manner for an intended operation such as disinfection and optical communication, (7) enable easy and convenient access to operational components for repair and maintenance, (8) include a mobile body having a center of mass proximate to its geometrical center for stability during movements, (9) move the mobile body autonomously while rotating the germicide sources, (10) enable operationally attaching an external peripheral component such as a handheld device thereto, and (11) provide for better cooling of the operational components during operation.

In some other embodiments, the projection device 100 may operate, or undergo inhibited operation with or without a complete halt, in response to one or more aspects of an external object or surface. Examples of such aspects (or object aspects) may include, but are not limited to, position, orientation, elevation, proximity or distance, size, dimensions, electrical input or output (e.g., voltage, current, resistance, pulse characteristics such as pulse width, duty cycle, amplitude, phase, frequency, shape, etc.), a type of electrical input or output (e.g., cumulative, additive, differential, referential, etc.), a type of non-electrical input or output (e.g., electromagnetic radiation such as UV light, infrared light, and visible light; a chemical agent, a physical agent, a biological agent, etc.), motion, direction, angle, range/proximity, and field of view. Further, the external object may be, wholly or in-part, active, stationary, mobile, wearable, and/or portable. The external object, in some examples, may be operationally coupled to a standalone or networked device in communication with the projection device 100. The networked device (e.g., via a sensor) may cause to operate, cease to operate, the projection device and/or exchange data therewith. In a further example, the external object may include a component or portion coupled to the projection device 100. For instance, the external object may include a first part attached to the projection device 100 and a second part operably coupled to the first part, where the second part may be located remote from the first part or the projection device 100. Other examples may include the external object including another device similar to the projection device 100.

Embodiments of the projection device 100 may also include a variety of known, related art, or later developed interface(s), including software interfaces (e.g., application programming interfaces, a graphical user interfaces, software ports, network sockets, etc.); hardware interfaces (e.g., cables, cable connectors, plugs, hardware ports and sockets, keyboards, magnetic or barcode readers, biometric scanners, interactive display screens, etc.); or both. The interface(s) may facilitate communication between various devices or components operationally coupled to the projection device 100. In some embodiments, the interface(s) may facilitate communication with computing devices such as those mentioned above.

The projection device 100 may also, independently or in communication with another device, have video, voice, or data communication capabilities (e.g., unified communication capabilities). For example, the projection device 100, or a remote device operationally coupled thereto, may include an imaging device (e.g., camera, printer, scanner, medical imaging device/system, etc.), an audio device (e.g., microphone, audio player, audio recorder, telephone, speaker, etc.), a video device (e.g., monitor/display screen, image projector, television, video recorder, etc.), and a sensor, or any other types of hardware commensurate with predefined or dynamically defined functions of the projection device 100, or a component thereof. Types of such sensor may include, but are not limited to, temperature sensors, proximity sensors (e.g., inductive, capacitive, photoelectric, ultrasonic, light detection and ranging (LIDAR), etc.), pressure sensors, chemical sensors, gas sensors, smoke sensors, level sensors, infrared sensors, image sensors, accelerometers, gyroscopes, optical sensors (e.g., dose sensors, intensity sensors, pulse sensors, etc.), and humidity sensors. The projection device 100 may additionally facilitate data transfer to a computing device or a computer readable medium (CRM).

As illustrated in FIGS. 1A-1B, in one embodiment, the projection device 100 may include a mobile body 108 and a projection head 110. The mobile body 108 may include a first lateral side 102-1, a second lateral side 102-2 (hereinafter collectively referred to as lateral sides 102), a front side 104, and a rear side 106. The lateral sides 102 may extend between the front side 104 and the rear side 106. The first lateral side 102-1 may be located opposite to the second lateral side 102-2. The lateral sides 102 may be separated by a sagittal plane SS' (shown in FIG. 2) passing therebetween. The sagittal plane SS' may pass through a center of the projection device 100, or components thereof such as the mobile body 108 and the projection head 110; however, other examples may include the sagittal plane SS' being off-centered. The sagittal plane SS' may extend from the rear side 106 to the front side 104 and divide the projection device 100, or the components therealong, into left and right parts. The mobile body 108 may include an assembly of parts configured to support, operate, and/or navigate the projection device 100 or any components thereof. The mobile body 108 may be adapted to traverse an intended path.

The mobile body 108 may include at least one mobility device operating to drive the projection device 100 along a path and/or over a surface. The mobility device may be motorized or non-motorized. The mobility device may be automated or configurable for manual operation. Any suitable type of mobility device may be contemplated to spatially move the projection device 100 based on any suitable motion principle known in the art including friction, magnetic or cryogenic levitation, and air-dependent or air-independent propulsion based on the path to be traversed. Examples of the mobility device may include, but are not limited to, a set of one or more wheels (e.g., omnidirectional wheels, caster wheels, etc.), a propeller, and an impeller. In one embodiment, as illustrated in FIGS. 1A-1B, the mobility device may be adapted as an autonomous vehicle 112 to spatially drive the projection device 100. The autonomous vehicle 112 may include rear motorized wheels (or drive wheels) and front non-motorized wheels (e.g., caster wheels). In some examples, the autonomous vehicle 112 may also implement turning mechanisms (e.g., an additional turning wheel positioned orthogonal to the drive wheels) to turn or rotate the projection device 100 about a vertical axis (e.g., a central or a lateral axis) of the autonomous vehicle 112 or the device 100. The autonomous vehicle 112 may include a platform (not shown) to mount or support various components of the projection device 100. In one example, the platform may be defined by a top surface of the autonomous vehicle 112; however, some examples may include the platform being defined by a surface lateral to the autonomous vehicle 112. Other examples may include the platform being a distinct component coupled to the autonomous vehicle 112.

The autonomous vehicle 112 may further include one or more types of sensors such as those mentioned above. In the illustrated example, the autonomous vehicle 112 includes a set of camera 114-1 and ultrasonic sensors 114-2, 114-3 (collectively referred to as front sensors 114), and another set of camera 116-1 and ultrasonic sensors 116-2, 116-3 (collectively referred to as rear sensors 116). The front sensors 114 and the rear sensors 116 may be positioned proximate to external surfaces, e.g., along the front side 104 and the rear side 106 respectively, of the projection device 100. The sensors 114, 116 may detect various aspects, including those noted above, of any external object proximate to the projection device 100 and assist in navigating the mobile body 108 along an intended path. The autonomous vehicle 112 may be operationally coupled to a control system of the projection device 100. The control system may operate alone or in combination with a remote computing device to control the autonomous vehicle 112. For example, the control system may communicate with the front sensors 114 and the rear sensors 116 to manipulate speed, a direction of motion or rotation, or any other operational parameters of the autonomous vehicle 112 based on any detected aspects of the external object or surface. The control system may include or couple to a power supply for powering the autonomous vehicle 112 and other components of the projection device 100. In one example, the power supply may include a battery (not shown) disposed in a battery compartment 118 (FIG. 1B) of the device 100. The battery may be positioned proximate to an exterior surface of the projection device 100 to provide easy access for charging, replacement, and/or maintenance.

In one embodiment, the mobile body 108 also includes a uniframe 300 serving as an integral frame to mount or support various operational components of the projection device 100. Examples of the operational components may include, but are not limited to, the projection head 110, a cooling system, and the control system including a controller 302. The uniframe 300 may be mounted on to the platform of the autonomous vehicle 112. The uniframe 300 may be positioned within a set of vertical planes including lateral exterior surfaces (hereinafter collectively referred to as exterior planes) of the autonomous vehicle 112 to ensure that a footprint of the projection device 100 is commensurate with dimensions of an intended path or surface to be traversed. In the illustrated embodiment of FIGS. 3-7, the uniframe 300 includes a base 304, a first column 306-1 and a second column 306-2 (hereinafter collectively referred to as columns 306), and a tray assembly 410 (shown in FIG. 4). The base 304 may have an H-shape defined by a central plate 308 attached between a first side plate 310-1 and a second side plate 310-2 (hereinafter collectively referred to as side plates 310). The side plates 310 may have approximately the same lengths (hereinafter referred to as side lengths); however, some examples may include the side plates 310 of different lengths. The side lengths may define a width of the uniframe 300 (or uniframe width $U_W$), and an extent between outer surfaces of the side plates 310 may define a length of the uniframe 300 (or uniframe length $U_L$). The uniframe width $U_W$ and the uniframe length $U_L$ may be set based on a supporting platform of a mobility device such as the autonomous vehicle 112 and a path to be traversed by the projection device 100. The central plate 308 may have a width (hereinafter referred to as plate width $P_W$) extending along a longitudinal axis of the side plates 310. The plate width $P_W$ may be relatively smaller than the uniframe width $U_W$. The plate width $P_W$ may depend on a number and type(s) of components and/or compartments to be arranged with or proximate to the central plate 308.

In the illustrated example, the central plate 308 has a first lateral surface and a second lateral surface (hereinafter collectively referred to as lateral surfaces). The lateral surfaces (not shown) may extend longitudinally between the side plates 310. The lateral surfaces may have lengths (hereinafter referred to as plate length $P_L$) depending on a supporting platform of a mobility device such as the autonomous vehicle 112. Each of the lateral surfaces along with proximate inner surfaces of the side plates 310 may define a cutout region formed due to the plate width $P_W$ being relatively smaller than the uniframe width $U_W$. The cutout region may allow the uniframe 300 to accommodate additional components without exceeding the uniframe width $U_W$ and hence, assist to keep the device footprint within the exterior planes. The lateral surfaces may include ridge plates 312 located within the respective proximate cutout regions. For example, the first lateral surface may be attached to a left ridge plate 312-1 and the second lateral surface may be attached to a right ridge plate 312-2. Each of the right ridge plate 312-2 and the left ridge plate 312-1 (collectively referred to as ridge plates 312) may have a similar geometry and/or dimensions for ease of construction. The ridge plates 312 may assist to support or restrict movement of an intended component (e.g., trays 412) of the projection device 100, discussed below in greater detail. The ridge plates 312 and the side plates 310 may be permanently attached, detachably secured, or formed integral to the base 304 using any suitable connection mechanisms known in the art including, but are not limited to, welding, nut and bolt, and gluing.

Further, the base 304 supports the columns 306 attached thereto. The columns 306 may be arranged perpendicular to the base 304; however, some examples may include one or more of the columns 306 being tilted relative to the base 304 depending on an intended separation between them. The first column 306-1 may be attached to the first side plate 310-1 and may define a front section 350-1 of the uniframe 300. The front section 350-1 may be disposed proximate to the front side 104 of the mobile body 108. The second column 306-2 may be attached to the second side plate 310-2 and may define a rear section 350-2 of the uniframe 300. The rear section 350-2 may be disposed proximate to the rear side 106 of the mobile body 108. The columns 306 may be positioned opposite to each other in the same vertical plane; however, some examples may include the columns 306 being located at least partially in different vertical planes. The columns 306 may have similar geometries and dimensions for ease of construction and intended stability of the uniframe 300. For the sake of brevity, constructional aspects of the first columns 306-1 are discussed here in detail; however, one having ordinary skill in the art would understand that the remaining column 306-2 may be made to have relatively similar constructional aspects including any required variations within the scope and spirit of the present disclosure.

Figure 3:
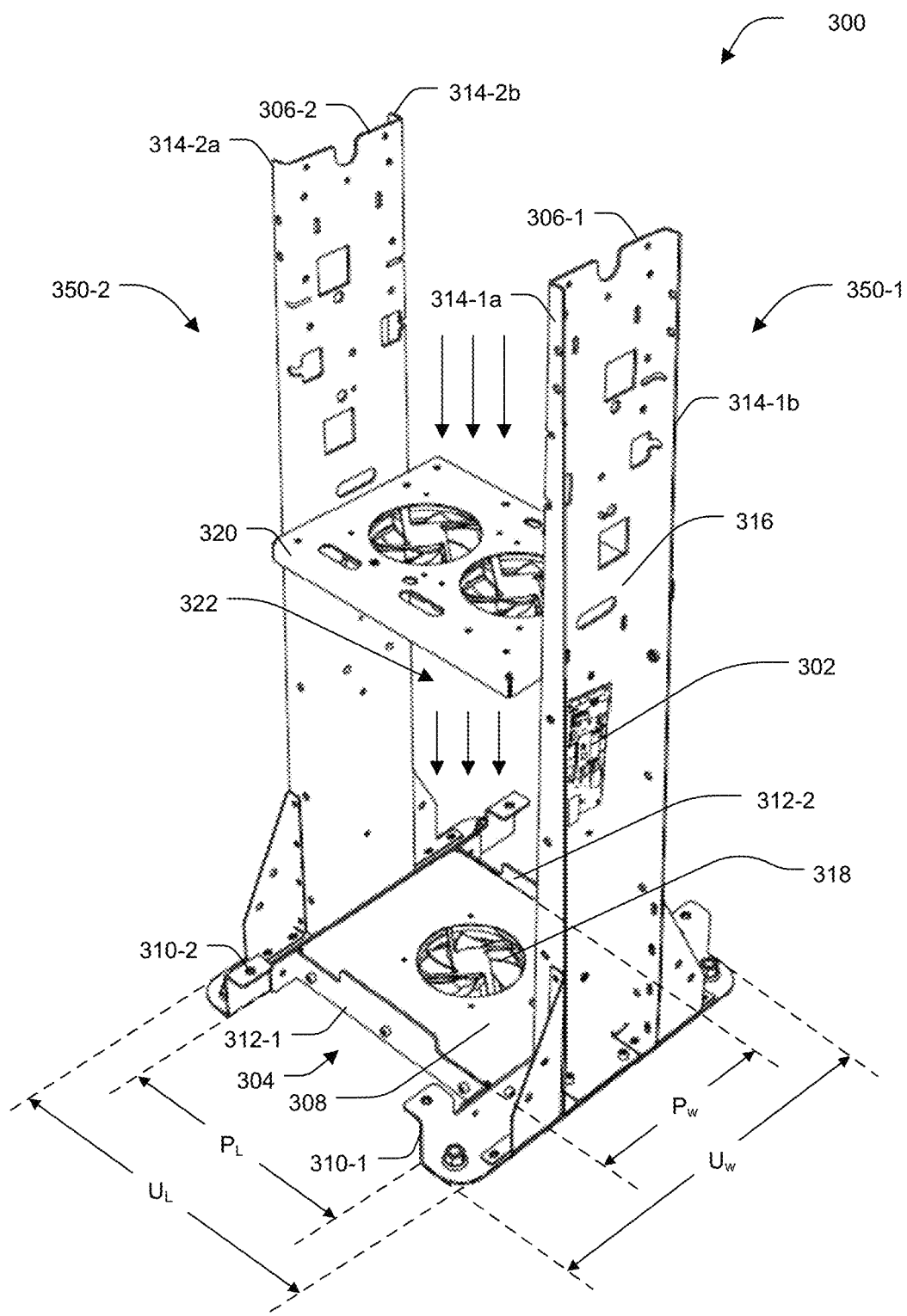
FIG. 3 is a front perspective view of an exemplary uniframe including a cooling system for the projection device of FIG. 1A, according to an embodiment of the present disclosure.

In one embodiment, the columns 306 may include flanges arranged laterally thereto. In one example, as illustrated in FIG. 3, the first column 306-1 includes a first left flange 314-1a and a first right flange 314-1b (hereinafter collectively referred to as first flanges 314-1). Similarly, the second column 306-2 may have a second left flange 314-2a and a second right flange 314-2b (hereinafter collectively referred to as second flanges 314-2). Both the first flanges 314-1 and the second flanges 314-2 (hereinafter collectively referred to as column flanges 314) may extend outwardly and away from the base 304. The first flanges 314-1 may form a first U-channel 316 with an outer surface of the first column 306-1. Similarly, the second flanges 314-2 may form a second U-channel (not shown) with an outer surface of the second column 306-2. The first U-channel 316 and the second U-channel may accommodate additional components and assist in maintaining a footprint of the mobile body 108 within the exterior planes of the autonomous vehicle 112. In one example, the first U-channel 316 may removably secure the controller 302 in the front section 350-1 of the uniframe 300 and the second U-channel may removably secure the battery (not shown) in the rear section 350-2 of the uniframe 300. Moreover, the column flanges 314, or the columns 306, may be tapered to have a lower portion being relatively broader than a corresponding upper portion. The tapering provides a relatively larger surface area in the lower portion and assists, along with the H-shaped base 304, in establishing a center of mass of the mobile body 108 towards a geometrical center thereof to improve stability and prevent tipping during movements. The column flanges 314 may be permanently attached, detachably secured, or formed integral to the respective columns 306 using any suitable connection mechanisms known in the art.

Further, the uniframe 300 may include or support additional components of the projection device 100. For example, the uniframe 300 may support the cooling system between the columns 306. The cooling system may include a heat sink 318 and a cooling panel 320. In one instance, the heat sink 318 (e.g., an active heat sink including a fan or a passive heat sink, or a combination thereof) may be embedded into an opening in the central plate 308 of the base 304. The heat sink 318 may be arranged in fluidic communication with the cooling panel 320 to expel heat from the projection device 100 during operation. The cooling panel 320 may be removably attached to the columns 306 at a preset minimum elevation point from the base 304 or the ground. The minimum elevation point may depend on a number and types of components and/or compartments under the cooling panel 320. In one example, the minimum elevation point may be located at a height of approximately 30 inches (or 76 centimeters) from the ground; however, other examples may include such height being greater or lesser than 30 inches. Further, the cooling panel 320 of some embodiments may be made to slide between the columns 306 for moving above the minimum elevation point. Other embodiments may include the cooling panel 320 being rotatable about a set axis extending along a transverse plane TT'. In some examples, the set axis may be perpendicular to the sagittal plane SS' of the device 100.

As shown in FIG. 4, the transverse plane TT' may intersect with the sagittal plane SS' and divide the uniframe 300, and the mobile body 108, into an upper section 402 and a lower section 404. The transverse plane TT' may extend horizontally through the minimum elevation point and across the lateral sides 102 of the mobile body 108. The upper section 402 may include the cooling panel 320; however, some examples may include the cooling panel 320 being positioned in the lower section 404. Above the cooling panel 320, the uniframe 300 may define a utility space 406 (FIG. 5) between the columns 306, e.g., in the upper section 402, to accommodate one or more components (such as the projection head 110) of the projection device 100, discussed below in further detail. Further, the cooling panel 320 may be disposed over the heat sink 318 to facilitate an airflow through an interior portion 322 therebetween within the uniframe 300. In one example, the cooling panel 320 may create a positive airstream into the interior portion 322 and the heat sink 318 may create a negative airstream moving away from the interior portion 322 for a substantially downward airflow (shown by downward arrows in FIG. 3) to remove heat from projection device 100 during operation. Other examples may include such positive and negative airstreams being created by any of the cooling panel 320 and the heat sink 318 for creating an airflow into or out of the interior portion 322 in the lower section 404 of the uniframe 300.

In one embodiment, as illustrated in FIGS. 4-7, the lower section 404 of the uniframe 300 may include the tray assembly 410 for carrying one or more operational components of the projection device 100. The tray assembly 410 may be positioned under the cooling panel 320. In one example, the tray assembly 410 includes a first tray 412-1 and a second tray 412-2 (collectively referred to as trays 412) and a hinge assembly (not shown). The trays 412 may be disposed between the columns 306 and lateral to the front section 350-1, or the rear section 350-2, of the uniframe 300. The trays 412 may be positioned on opposite sides of the columns 306 across the sagittal plane SS'. For example, the first tray 412-1 may be positioned proximate to the first lateral side 102-1 and the second tray 412-2 may be positioned proximate to the second lateral side 102-2 of the mobile body 108, or the projection device 100.

The trays 412 may have a similar geometry and/or dimensions for ease of construction and stability of the uniframe 300. For the sake of brevity, constructional aspects of only one of the trays 412 are discussed here in detail; however, one having ordinary skill in the art would understand that the remaining tray may also have relatively similar constructional aspects including any required variations within the scope and spirit of the present disclosure. In the illustrated example of FIG. 5, the first tray 412-1 may have an interior tray surface (not shown) and an opposing exterior tray surface 414. The interior tray surface of the first tray 412-1, similar to an interior tray surface 416 of the second tray 412-2, may provide a space to mount or support various operational components of the projection device 100. For instance, the first tray 412-1 may carry low voltage components and the second tray 412-2 may carry high voltage components, or vice versa in other examples, on the respective interior surfaces. On the other hand, the exterior tray surface 414 may include an upper tray handle 418-1 and a lower tray handle 418-2 (hereinafter collectively referred to as tray handles 418). The tray handles 418 may assist to manipulate and support the trays 412 in different positions, discussed below in further detail. The second tray 412-2 may also include tray handles (not shown) similar to the tray handles 418.

The trays 412 may be pivotably attached to the lower section 404 using the hinge assembly (not shown) to transition between a closed position and an open position. The hinge assembly may be arranged with the base 304 and/or the columns 306 along a bottom portion of the trays 412. In one embodiment, the hinge assembly may include a rod (not shown) extending parallel to a horizontal axis in the sagittal plane SS'. The rod may be movably connected to the corresponding tray, such as the first tray 412-1, via movable or non-movable brackets (not shown). Other suitable types of hinge assembly known in the art can also be contemplated including a roller pin assembly. In some embodiments, the hinge assembly may also include aspects (e.g., gears, rollers, ribs, levers, magnets, etc.) to lock the trays 412 in one or more positions between the closed position and the open position. The hinge assembly may include portions permanently attached, detachably secured, or formed integral to the uniframe 300 and/or the tray assembly 410. In the closed position (FIG. 4), the trays 412 may be arranged parallel to a vertical axis of the projection device 100 such that the respective interior tray surfaces carrying the operational components may be perpendicular to the base 304 and orient towards each other. Such vertically-arranged trays 412 may have a predefined separation therebetween in the closed position. This separation may include the interior portion 322 of the uniframe 300 under the cooling panel 320. Hence, unlike traditional support frames providing for horizontal stacking of operational components on top of each other, such vertical arrangement of operational components with the trays 412 in the closed position enables an unobstructed airflow through the interior portion 322 for efficient cooling of the operational components during operation.

As illustrated in FIG. 5, the trays 412 may be manipulated to transition from the closed position to the open position, and vice versa. For example, the tray handles 418, such as the upper tray handle 418-1, may be used to pull the trays 412 outward from the uniframe 300. Upon being manipulated, the trays 412 may pivot about a pivoting axis defined by a longitudinal axis of a component (e.g., such as the rod) of the hinge assembly connected to the respective trays 412. The trays 412 may pivot to at least partially extend out from one of the lateral sides 102 of the mobile body 108, or the projection device 100, for opening up. In the open position, the trays 412 may extend up to a maximum pivot angle relative to the pivoting axis or a horizontal axis in the sagittal plane SS'. The maximum pivot angle of the trays 412 may be controlled by the corresponding lower tray handle 418-2. For example, as shown in FIG. 5, the lower tray handle 418-2 may engage with a ridge plate, such as the left ridge plate 312-1, of the base 304 to limit the maximum pivot angle of the first tray 412-1 in the open position. Similarly, the second tray 412-2 may also include a lower tray handle (not shown), similar to the lower tray handle 418-2, engaging with the right ridge plate 312-2 to limit the maximum pivot angle of second first tray 412-2 in the open position. Hence, the lower tray handle, such as the lower tray handle 418-2, may assist in controlling an outward (or lateral) extension of the corresponding tray, such as the first tray 412-1, to prevent such tray from inadvertently falling out and/or hit any adjacent surfaces to jeopardize operational safety, e.g., when the mobile body 108, or the projection device 100, may be traversing a narrow path such as an aircraft aisle. In one example, the maximum pivot angle may be 45 degrees relative to the vertical axis; however, other examples may include the maximum pivot angle being increased (e.g., up to approximately 90 degrees) or decreased (e.g., up to approximately 35 degrees) based on dimensions of the ridge plates 312 and heights of the proximate lower tray handles. Some embodiments may also include the height of the lower tray handles, such as the lower tray handle 418-2, being adjustable for on-demand change in the maximum pivot angle of the corresponding trays 412.

Each of the trays 412 may have a predefined tray length, tray width, and tray depth. The tray length may refer to a tray extension between the base 304 and the minimum elevation point. The tray width may refer to a tray extension between the columns 306 (or the side plates 310) of the base 304. The tray depth may refer to a tray extension between the columns 306 and a ridge plate of the base 304 proximate thereto. Both the trays 412 may have approximately the same tray dimensions (e.g., tray length, tray breadth, and tray depth); however, some examples may include the trays 412 having different tray dimensions. In some other examples, the tray dimensions may be proportionate to each other. For instance, the tray length may be at least approximately 1.2 times the tray breadth and/or at least approximately 8 times the tray depth depending on the minimum elevation point. In further examples, at least one of the trays 412 may be removable, partitioned/partitionable, and/or formed out of multiple trays 412 being integrally or removably joined together. Moreover, in some examples, the trays 412 may be removably attached to respective support plates pivotably attached to the uniframe 300. Other examples may include the trays 412 being coupled to a linear or rotary actuator (not shown) in the hinge assembly, where such actuator may be driven by the control system to automate transitioning of the trays 412 between the closed and open positions.

The lower section 404 of the uniframe 300 may also include or support the control system including the power supply and the controller 302 for controlling various components of the projection device 100. The controller 302 may be positioned in the lower section 404; however, some examples may include one or more components (e.g., a driver circuit or trigger circuit for one or more germicide sources, etc.) of the control system being located in the upper section 402. In one embodiment, the power supply such as the battery may be disposed proximate to the rear side 106 of the projection device 100 and the controller 302 may be arranged proximate to the front side 104 of the projection device 100 to provide easy of access for maintenance and replacement. However, in some examples, the controller 302 may be positioned proximate to the battery on the same side, such as the front side 104 or the rear side 106, of the mobile body 108.

The controller 302 may correspond to an electrical or electronic component operating to control predefined or dynamically defined functions and movements of various components including, but not limited to, the tray assembly 410, the mobile body 108, the projection head 110, and any peripheral components operationally coupled to the projection device 100. Aspects of the controller 302, in some examples, may also include or couple to mechanical components, such as the actuator, of the projection device 100. In some embodiments, the controller 302 may include or be implemented by way of a single device (e.g., a computing device, a processor or an electronic storage device) or a combination of multiple devices. The controller 302 may be implemented in hardware or a suitable combination of hardware and software. The controller 302 may include, for example, microprocessors, microcomputers, microcontrollers, digital signal processors, central processing units, state machines, logic circuits, and/or any devices that may manipulate signals based on operational instructions. Among other capabilities, the controller 302 may be configured to fetch and execute computer readable instructions in communication with a storage device (not shown). The storage device may be configured to store, manage, or process data in a database related to operations of the projection device 100 and a log of profiles of various devices coupled to the controller 302 and associated communications including instructions, queries, data, and related metadata. The storage device may include any computer-readable medium known in the art, related art, or developed later including, but not limited to, a processor or multiple processors operatively connected, a volatile memory, a non-volatile memory, and a disk drive. Further, the controller 302 may include or operate in communication with one or more interfaces, such as those mentioned above.

The controller 302 may be configured to control various components, such as the autonomous vehicle 112, the projection head 110, and the tray assembly 410, of the projection device 100 based one or more predefined or dynamically defined operational modes, discussed in detail below. The controller 302, in some examples, may operate in communication with a software product configured to control one or more aspects of the projection device 100. The software product may include one of an operating system, a computer application, and a device driver loaded on a computer readable medium including those mentioned above. In some examples, the software product may include or communicate with a software patch operating to modify or assist in implementing an aspect (e.g., installation, uninstallation, synchronization, general or specialized operation, etc.) of the software product or that of the projection device 100. The software product, alone or in combination with the software patch, may assist to adjust a value of an operating parameter of a component or a device associated with the projection device 100 for modulating a corresponding output. For instance, the software product may provide an interface between the controller 302 and a trigger circuit (not shown) of the projection head 110. The trigger circuit may include a trigger sensor (e.g., variable resistor or potentiometer) to assist in manipulating an input voltage being applied to the projection head 110 based on a control signal from the controller 302. The software product may interpret a sensor signal from the trigger sensor to cause the controller 302 into providing the control signal that drives the trigger circuit to adjust the applied input voltage. Hence, in one example, the software product may assist in increasing an input voltage for increasing a first value (e.g., 2 KV) thereof to a second value (e.g., 3 KV) for improving an intensity or dose of the projected germicide. Other examples of the operating parameters may include, but are not limited to, operational duration or cycle, pulse frequency, toggling rate, output voltage, input or output (I/O) currents, I/O resistances, polarity, direction of rotation or motion, and operational modes. In some instances, the software patch may inhibit an operation of a component of the projection device 100 and/or the software product. Both the software patch and the software product may be installed on the same computing device operationally coupled to the projection device 100; however, other examples may include the software product and the software patch being installed on different computing devices, e.g., including a remote device.

Figure 7:
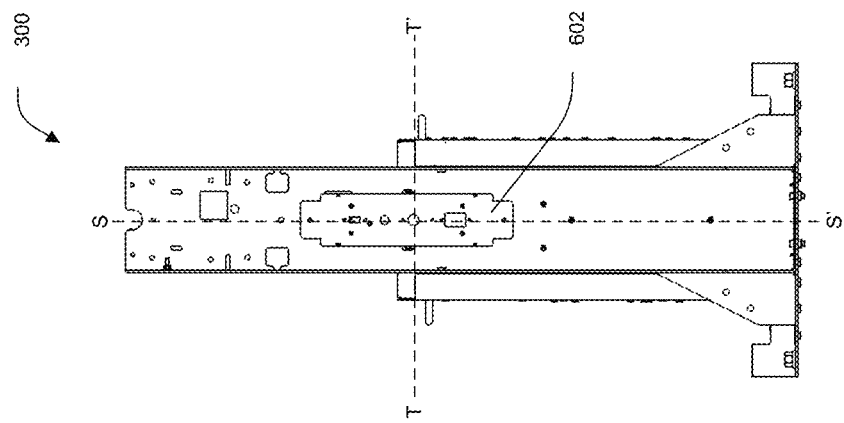
FIG. 7 is a rear elevation view of the uniframe of FIG. 4 including the auxiliary frame of FIG. 6, according to an embodiment of the present disclosure.
Figure 6:
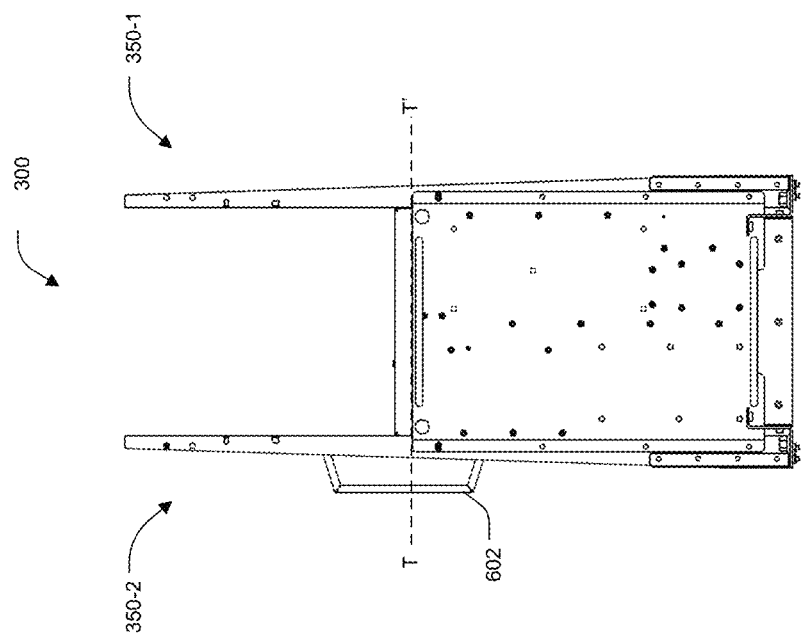
FIG. 6 is a left elevation view of the uniframe of FIG. 4 including an exemplary auxiliary frame, according to an embodiment of the present disclosure.

In a further embodiment, the lower section 404 may include or support an auxiliary frame 602. As illustrated in FIGS. 6-7, the auxiliary frame 602 may be attached to the second column 306-2 in the rear section 350-2 of the uniframe 300. The auxiliary frame 602 may be aligned vertically (or horizontally in some examples) relative to the transverse plane TT' and/or the cooling panel 320 and extend outwardly away from the uniframe 300. The auxiliary frame 602 may have a fixed geometry; however, some examples may include the auxiliary frame 602 having portions made to selectively collapse or retract relative to the uniframe 300. The auxiliary frame 602 may be disposed within (i) vertical planes including the lateral sides 102 of the mobile body 108, or (ii) the exterior planes of the autonomous vehicle 112, to avoid exceeding a width of a path to be traversed by the projection device 100. The auxiliary frame 602 may include ports (not shown) coupled to the control system. The ports may assist to operationally couple one or more peripheral components or devices to the projection device 100. For instance, the auxiliary frame 602 may assist in connecting a handheld device with the control system.

As illustrated in FIG. 8, in one example, a handheld projection device 802 may be coupled to the control system via the auxiliary frame 602. The handheld projection device 802 may include a UV source 804 to project UV light and a power cable 806 having a suitable length based on surfaces to be accessed for disinfection. The cable 806 may be removably attached to the auxiliary frame 602. Upon being attached, the handheld projection device 802 may be powered by the battery and controlled via the controller 302 of the control system. In some examples, the handheld projection device 802 may be cableless to operationally connect with the controller 302 via a transceiver (not shown) attached to the auxiliary frame 602. The controller 302 may drive the handheld projection device 802 to project the UV light for surface disinfection based on selection or de-selection of one or more operational modes of the projection device 100, discussed below in further detail. The controller 302 along with the uniframe 300 and the auxiliary frame 602 may be covered by a casing of the mobile body 108.

In one embodiment, the mobile body 108 may include one or more cover panels defining one or more casings to protect one or more components of the projection device 100 from dust and damage. Such casings may also assist to improve aesthetics of the projection device 100. In one example, as shown in FIG. 8, the mobile body 108 may include a lower casing 808-1 formed out of a single panel or a set of panels to surround one or more components (e.g., the tray assembly 410, the controller 302, a portion of the auxiliary frame 602, etc.) in the lower section 404 of the uniframe 300. For instance, the lower casing 808-1 may extend along the rear section 350-2 of the uniframe 300 to define the battery compartment 118 therewith along the rear side 106 of the mobile body 108. The lower casing 808-1 may be removably secured to the columns 306 in the lower section 404; however, some portions of the lower casing 808-2 may be additionally, or alternatively, secured to the autonomous vehicle 112. In addition to the lower casing 808-1, the mobile body 108 may include cover panels 808-2a and 808-2b collectively defining an upper casing 808-2 of the uniframe 300. The cover panels 808-2a, 808-2b may be secured to the first column 306-1 and the second column 306-2 respectively in the upper section 402 of the uniframe 300. The cover panels 808-2a, 808-2b may be separated from each other to substantially maintain the utility space 406 between the columns 306 in the upper section 402. The upper casing 808-2 and the lower casing 808-1 (hereinafter collectively referred to as casings 808) may be made up of any rigid, durable, fire-retardant, or fire-resistant materials known in the art, related art, or developed later including, but not limited to, metals, polymers, alloys, and glass, or any combinations thereof.

The upper casing 808-2 may further include or support one or more components of the mobile body 108. In one embodiment (FIG. 8), the upper casing 808-2 may include or support a first drive handle 810-1 and a second drive handle 810-2 (hereinafter collectively referred to as drive handles 810). The drive handles 810 may assist a user to manually maneuver the projection device 100 or the mobile body 108 from one position, or orientation, to another. In another embodiment, the upper casing 808-2 may additionally include a display unit (not shown) positioned along the rear side 106 of the mobile body 108; however, some embodiments may include the display unit being located remote from the upper casing 808-2 or the projection device 100. The display unit may independently or in communication with a user interface (not shown) may indicate information pertaining to an operation of the projection device 100. In one example, the display unit may represent or include an interactive display screen operating as an input device for enabling an operator to access, control, or dynamically define different functions of the projection device 100. In another example, the display unit may display a dashboard providing a list of functions, modes, parameters, avatars, operational aspects, etc. that the operator may select or modify for a desired operation of the projection device 100. The operational aspects may relate to any predefined or dynamically defined tasks related to a functionality and/or administration of the projection device 100, or a corresponding component(s) thereof. Examples of these aspects may include, but are not limited to, (i) values of operational parameters such as frequency, wavelength, duration, energy, and dose, (ii) a selected mode in operation, (iii) operational states of different components, (iv) statuses of various operational tasks such as disinfection and navigation, and so on.

In a further embodiment (FIG. 9), the upper casing 808-2 may include or couple to a transparent housing 902 that may surround (or envelop) the upper section 402 including the utility space 406 therein. The housing 902 may be made up of any suitable material (e.g., quartz glass) or include an arrangement (e.g., wire mesh, holes, etc.) that may be substantially rigid. The housing 902 may be made transparent or include portions that are optically permeable to UV light. These portions may extend along surfaces intended for being irradiated with the UV light. In some examples, the housing 902 may include, or operate as, an optical filter to pass, or block, an intended wavelength of light (e.g., a specific UV wavelength such as UVC, visible light, etc.) therethrough. The housing 902 may be removably secured with portions of the casings 808 and/or the columns 306 in the upper section 402; however, some examples may include portions of the housing 902 being formed integral to the upper casing 808-2. The housing 902 may be supported by the opposing lateral sides 102 of the mobile body 108, or the projection device 100. Proximate to the upper casing 808-2, the projection device 100 may further include the projection head 110 positioned within the utility space 406 in the upper section 402 of the uniframe 300.

In one embodiment, the projection head 110 may be operated by the controller 302 to, at least one of, (1) directionally project the germicide towards surfaces above and proximate to the opposing lateral sides 102 of the projection device 100, (2) alternately tilt (or rotate) about a horizontal axis in the sagittal plane SS' to project the germicide towards the surfaces, and (3) alternately tilt (or rotate) in opposite directions across the sagittal plane SS'. The projection head 110 may be implemented in a closed configuration or an open configuration (hereinafter collectively referred to as head configurations). In some embodiments, the projection head 110 in the closed configuration may be implemented on the handheld projection device 802.

Figures 10, 11:
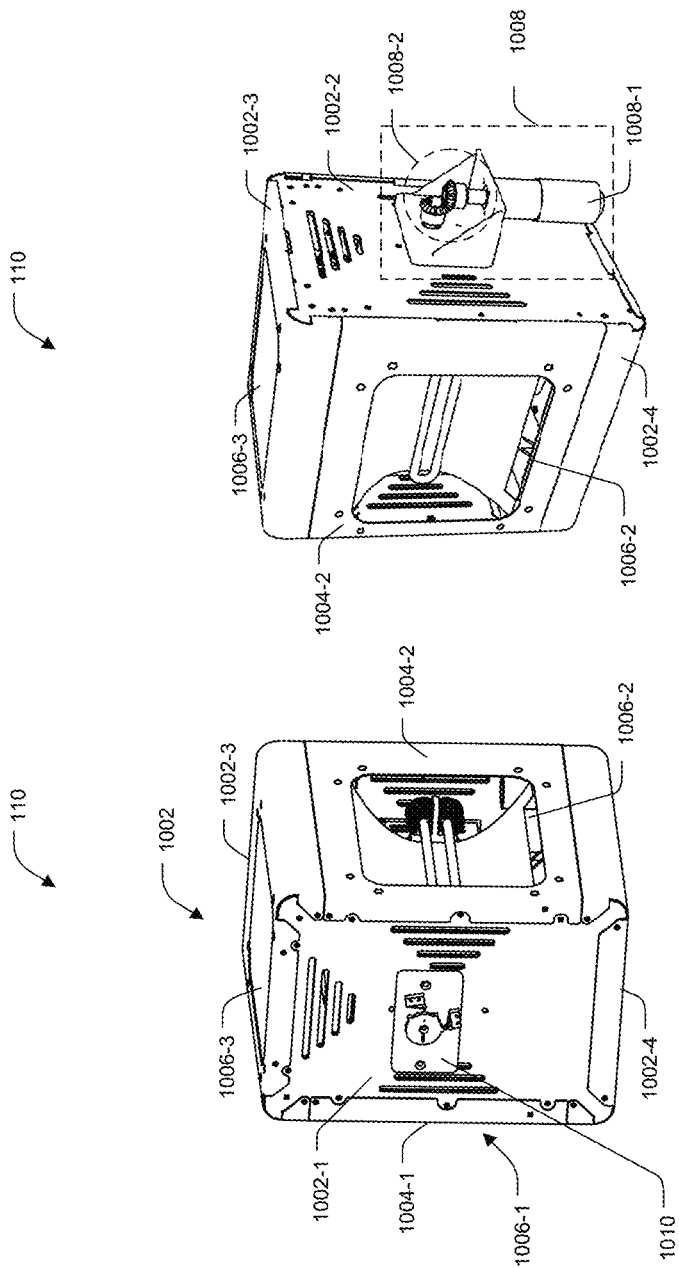
FIG. 10 is a front perspective view of an exemplary projection head in a closed configuration coupled to a rotation assembly for the projection device of FIG. 1A, according to an embodiment of the present disclosure.
FIG. 11 is a rear perspective view of the projection head of FIG. 10, according to an embodiment of the present disclosure.

In the closed configuration, as illustrated in FIGS. 10-11, the projection head 110 may include a lamp housing 1002 configured to carry components operating to project the germicide. The lamp housing 1002 may include a front plate 1002-1, a rear plate 1002-2, a top plate 1002-3, and a bottom plate 1002-4. The lamp housing 1002 may also include a first lateral plate 1004-1 and a second lateral plate 1004-2 (hereinafter collectively referred to as lateral plates 1004) extending between the front plate 1002-1 and the rear plate 1002-2. In the illustrated example, the first lateral plate 1004-1, the second lateral plate 1004-2, and the top plate 1002-3 includes a first window 1006-1, a second window 1006-2, and a third window 1006-3 (hereinafter collectively referred to as windows 1006) respectively. The windows 1006 may be made optically permeable to at least UV light using openings and/or any suitable materials known in the art including glass, quartz, and polymers. The front plate 1002-1, the rear plate 1002-2, and the bottom plate 1002-4 of the lamp housing 1002 may be made opaque to block UV the germicide such as UV light and support operational components of the projection head 110. The lamp housing 1002 may be made of any suitable materials known in the art including, but not limited to, metals, polymers, glass, quartz, alloys, or a combination thereof that may be sufficiently rigid and sturdy to support the operational components.

As illustrated in FIGS. 10-11, the lamp housing 1002 may be attached to a rotation assembly including a driver assembly 1008, a sensor block 1010, and a shaft 1012 (shown in FIG. 12) connected therebetween. The driver assembly 1008 may include a motor 1008-1 and a bevel-gear arrangement 1008-2 for rotating the shaft 1012; however, any other suitable mechanisms known in the art may be implemented. The shaft 1012 may pass through the lamp housing 1002 and have one end attached to the bevel-gear arrangement 1008-2. The other end of the shaft 1012 may be attached to the sensor block 1010 operating in communication with the controller 302. The sensor block 1010 may be attached to an exterior of the front plate 1002-1 and the driver assembly 1008 may be attached to an exterior of the rear plate 1002-2 of the lamp housing 1002. Further, the shaft 1012 may operate to support and rotate the projection head 110 with the lamp housing 1002 in the closed configuration. However, in the open configuration (shown in FIG. 9 and FIG. 14), the projection head 110 may be implemented without a dedicated housing such as the lamp housing 1002. For example, the upper casing 808-2 may include, or be implemented as, a stationary housing such as the housing 902, which may be disconnected or distanced from the projection head 110 and the rotation assembly. The upper casing 808-2 or the housing 902 may remain stationary relative to the projection head 110 during rotations of the shaft 1012. Each of the head configurations may include the projection head 110 having a lamp assembly 1200 to project the germicide such as UV light.

Figures 12, 13:
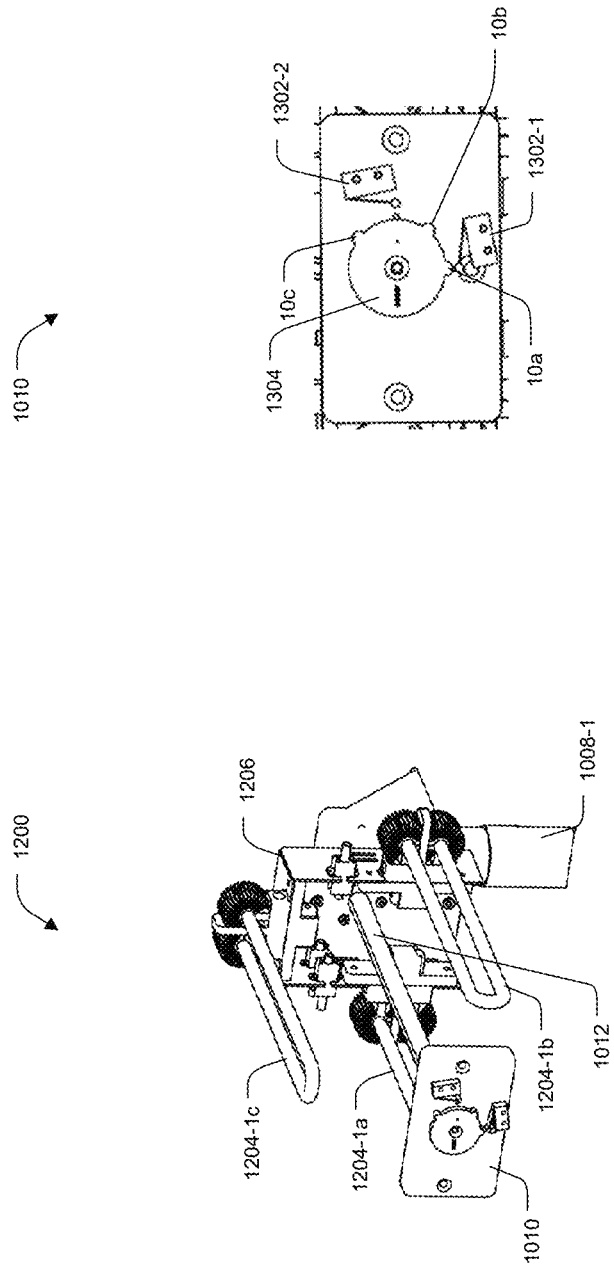
FIG. 12 is a front perspective view of an exemplary lamp assembly without reflectors and coupled to the rotation assembly for the projection head of FIG. 10, according to an embodiment of the present disclosure.
FIG. 13 illustrates an exemplary sensor block for the rotation assembly of FIG. 10 and FIG. 12, according to an embodiment of the present disclosure.

As illustrated in FIG. 12, the lamp assembly 1200 may include a first radiation source 1204-1a, a second radiation source 1204-1b, and a third radiation source 1204-1c (hereinafter collectively referred to as radiation sources 1204-1) operating to emit UV light. However, some examples may include the lamp assembly 1200 having additional components operating to emit other types of germicides such as those mentioned above. The radiation sources 1204-1 may be secured to a bracket 1206 for connecting to the rotation assembly. For example, the bracket 1206 may be attached to the shaft 1012 passing therethrough. One end of the shaft 1012 may be attached to the driver assembly 1008 (e.g., rear to the bracket 1206) and an opposing end of the shaft 1012 may be attached to the sensor block 1010 (e.g., towards a front of the lamp assembly 1200 opposing the bracket 1206). As illustrated in FIG. 13, the sensor block 1010 may include a first contact sensor 1302-1, a second contact sensor 1302-2 (hereinafter referred to as contact sensors 1302) and a rotatable contact ring 1304 proximate thereto. The contact ring 1304 may include a first contact pin 10a, a second contact pin 10b, and a third contact pin 10c (hereinafter collectively referred to as contact pins 10). The contact ring 1304 may be rotated by the shaft 1012 to engage the contact pins 10 with the contact sensors 1302 for indicating a position or a direction of rotation of the projection head 110.

Further, the bracket 1206 may be attached directly to the driver assembly 1008 in the open configuration of the projection head 110; however, the closed configuration may include the bracket 1206 being coupled to the driver assembly 1008 via the lamp housing 1002, as discussed above. On the bracket 1206, the radiation sources 1204-1 may be arranged around the shaft 1012 with the first radiation source 1204-1a and the second radiation source 1204-1b located in a common plane, and the third radiation source 1204-1c positioned therebetween in a different plane. The radiation sources 1204-1 may include, or be implemented as, a bulb, a light emitting diode (LED), a Xenon UV lamp, or any other types of radiation sources known in the art. The radiation sources 1204-1 may be pulsed radiation sources, continuous radiation sources, or a combination thereof, driven by the control system or the controller 302. For example, the pulsed radiation sources may be configured by the controller 302 to emit pulses of UV light of a predetermined energy or intensity at a predefined or dynamically defined pulse frequency and within a predetermined wavelength range. On the other hand, the continuous radiation sources may be configured by the controller 302 to emit a continuous stream of UV light. In some examples, the continuous radiation sources may be turned on and off at a predetermined frequency (or pulse frequency) by the controller 302 to emit pulses of UV light. Further, the controller 302 may configure the radiation sources 1204-1 to irradiate timed pulses of the UV light with each pulse having predefined characteristics such as energy, power, wavelength, and/or frequency. For example, the controller 302 may simultaneously drive each of the radiation sources 1204-1 at a predefined or dynamically defined pulse frequency to emit an intended amount of energy per pulse. In another example, the controller 302 may drive the radiation sources 1204-1 at a combined pulse frequency of at least 20 Hz to emit a predefined amount of energy. In yet another example, the controller 302 may drive at least two of the radiation sources 1204-1 at different frequencies. For instance, the energy per pulse may range from 30 to 150 Joules and the pulse frequency may range from 10 Hz to 60 Hz.

In one embodiment, the controller 302 may drive the radiation sources 1204-1 alternately to emit the UV light for same or different durations during the operational cycle. For example, the controller 302 may sequentially drive the third radiation source 1204-1c, followed by the first radiation source 1204-1a, and the second radiation source 1204-1b to emit the UV light within the operational cycle. In another example, the controller 302 may constantly drive the third radiation source 1204-1c to emit the UV light while alternately triggering the first radiation source 1204-1a and the second radiation source 1204-1b to emit the UV light. In yet another example, the controller 302 may constantly drive the first radiation source 1204-1a to emit the UV light while alternately triggering the second radiation source 1204-1b and the third radiation source 1204-1c to emit the UV light. In still another example, the controller 302 may constantly drive the second radiation source 1204-1b to emit the UV light while alternately triggering the first radiation source 1204-1a and the third radiation source 1204-1c to emit the UV light. In a further example, the controller 302 may switch-off at least one of the radiation sources 1204-1, for example, the third radiation source 1204-1c, while alternately triggering the remaining radiation sources 1204-1 to emit the UV light. The controller 302 may toggle or switch from driving one radiation source to another at a predefined or dynamically defined toggling rate to emit UV light within the operational cycle. In some embodiments, the toggling rate may be defined based on the pulse frequency and/or the energy per pulse associated with one or more of the radiation sources 1204-1.

Figure 14:
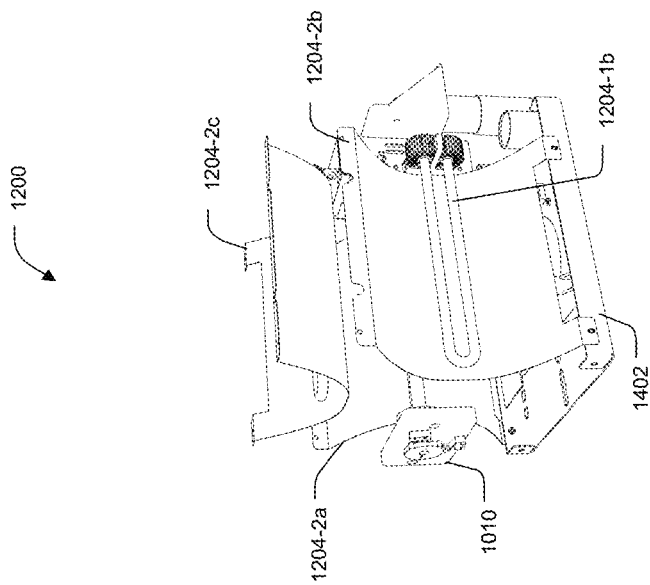
FIG. 14 is a front perspective view of the projection head of FIG. 10 in an open configuration including the lamp assembly of FIG. 12, according to an embodiment of the present disclosure.

The lamp assembly 1200, as illustrated in FIG. 14, additionally includes a first reflector 1204-2a, a second reflector 1204-2b, and a third reflector 1204-2c (hereinafter collectively referred to as reflectors 1204-2). The first reflector 1204-2a may be positioned behind the first radiation source 1204-1a to collectively define a first radiation unit 1204-a. The second reflector 1204-2b may be positioned behind the second radiation source 1204-1b to collectively define a second radiation unit 1204-b. The third reflector 1204-2c may be positioned behind the third radiation source 1204-1c to collectively define a third radiation unit 1204-c. The first radiation unit 1204-a, the second radiation unit 1204-b, and the third radiation unit 1204-c (hereinafter collectively referred to as radiation units 1204) may include respective reflectors 1204-2 being oriented to project the UV light in different directions or planes. For example, the first reflector 1204-2a, the second reflector 1204-2b, and the third reflector 1204-2c may be oriented to direct the UV light towards a first plane, a second plane, and a third plane (collectively referred to as projection planes) respectively. The first plane may be opposite (and parallel in some examples) to the second plane. In another example, the third plane may be orthogonal to at least one of the first plane and the second plane. Each of the reflectors 1204-2 may have a curved profile to provide a predefined field of view of projection (or projection angle) of approximately 45 degrees with respect to a longitudinal axis of the respective radiation sources 1204-1. The projection angle of approximately 45 degrees for the reflectors 1204-2 may assist to balance a trade-off between the surface coverage and the UV intensity at a set distance (e.g., approximately 1 meter) from the radiation units 1204; however, other examples may include the projection angle being greater or lesser than approximately 45 degrees.

Figure 15:
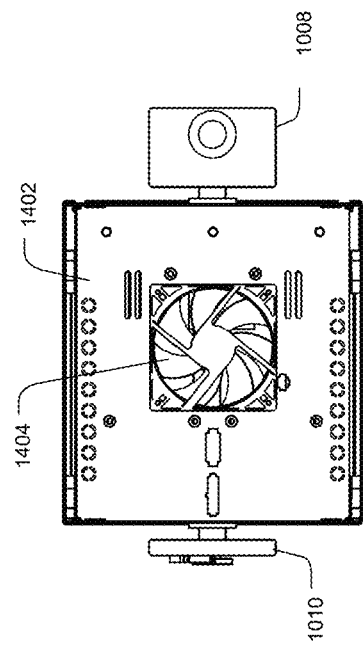
FIG. 15 is a bottom elevation view of the projection head of FIG. 10 including a cooling unit, according to an embodiment of the present disclosure.

Further, the lamp assembly 1200 may also include a supporting plate 1402 to support the reflectors 1204-2 with the bracket 1206. For example, the first reflector 1204-2a and the second reflector 1204-2b may be attached to the supporting plate 1402 and the bracket 1206. The third reflector 1204-2c may be attached to the bracket 1206 and located above the supporting plate 1402, the first reflector 1204-2a, and the second reflector 1204-2b. The lamp assembly 1200 including the supporting plate 1402, the radiation units 1204, and the bracket 1206 may collectively define the projection head 110 in the open configuration. Other examples may include the supporting plate 1402 including the bottom plate 1002-4 of the lamp housing 1002 in the closed configuration of the projection head 110. As illustrated in FIG. 15, the supporting plate 1402 (or the bottom plate 1002-4) may include a cooling unit 1404 (e.g., a fan, a vacuum pump, etc.) creating an airflow for cooling the radiation units 1204. In one embodiment, the cooling unit 1404 may create a suction airstream in the lamp assembly 1200 or the lamp housing 1002; however, other examples may include the cooling unit 1404 operating as a blower to create a positive airstream into the lamp assembly 1200 or the lamp housing 1002 for cooling the radiation units 1204 therein. The radiation units 1204 may be positioned proximate to the windows 1006 of the lamp housing 1002 to project the UV light therethrough in the closed configuration of the projection head 110. For example, the first radiation unit 1204-a may be positioned proximate to the first lateral plate 1004-1 with the first reflector 1204-2a oriented towards the first window 1006-1. Similarly, the second radiation unit 1204-b may be positioned proximate to the second lateral plate 1004-2 with the second reflector 1204-2b oriented towards the second window 1006-2. On the other hand, the third radiation unit 1204-c may be positioned proximate to the top plate 1002-3 with the third reflector 1204-2c oriented towards the third window 1006-3 of the lamp housing 1002. The radiation units 1204 may project the UV light through the respective windows 1006 towards target surfaces located exterior to the projection device 100. Such orientations and positioning of the radiation units 1204 may limit or prevent UV dispersion towards the front side 104 and the rear side 106, and assists to directionally project UV light towards the surfaces above and lateral to the projection head 110, or the projection device 100, for better energy management per surface to be disinfected.

In one embodiment, the projection head 110 including the lamp assembly 1200 may be rotatably mounted to the mobile body 108 via the rotation assembly. For example, the shaft 1012 may be rotatably mounted to the columns 306 such that the projection head 110 may be positioned within the utility space 406 above the cooling panel 320 in the uniframe 300. The mounted shaft 1012 may have a longitudinal axis extending along the horizontal axis in the sagittal plane SS' with the sensor block 1010 mounted to the first column 306-1 and the bracket 1206 mounted to the second column 306-2. The projection head 110 may be coupled to the shaft 1012 via the bracket 1206 and positioned on the uniframe 300 in the open configuration or the closed configuration, as discussed above.

Figure 16A:
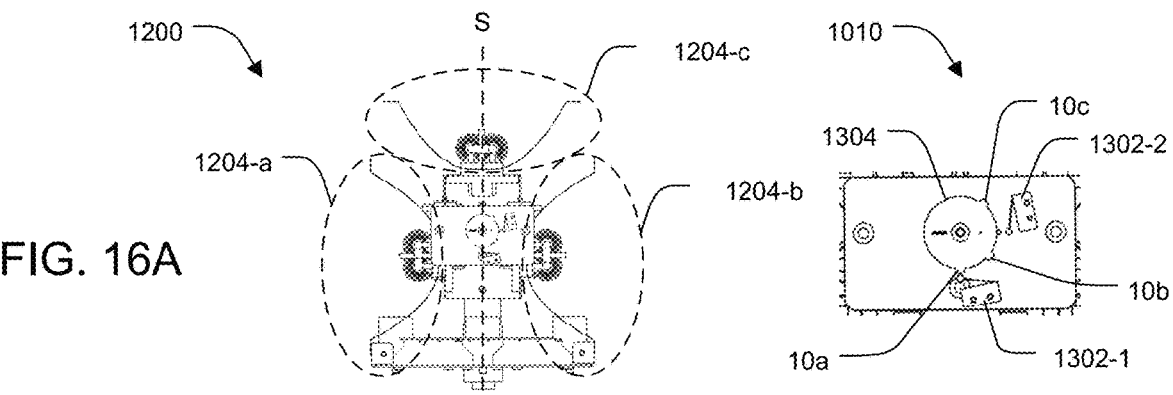
FIGS. 16A-16C illustrate an exemplary operation of the projection head of FIG. 14 for implementing the projection device of FIG. 1A, according to an embodiment of the present disclosure.
Figure 16B:
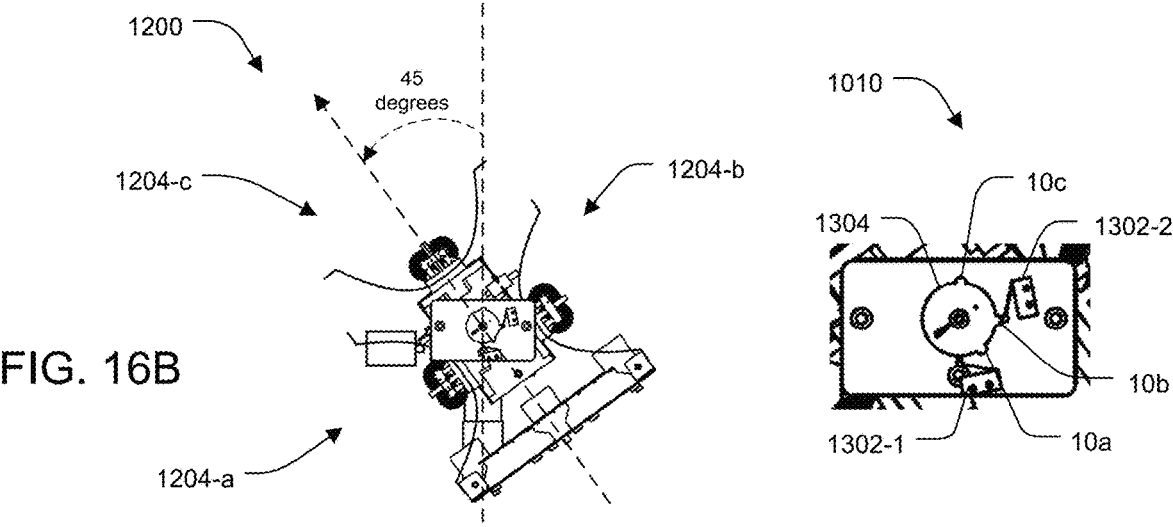
Figure 16C:
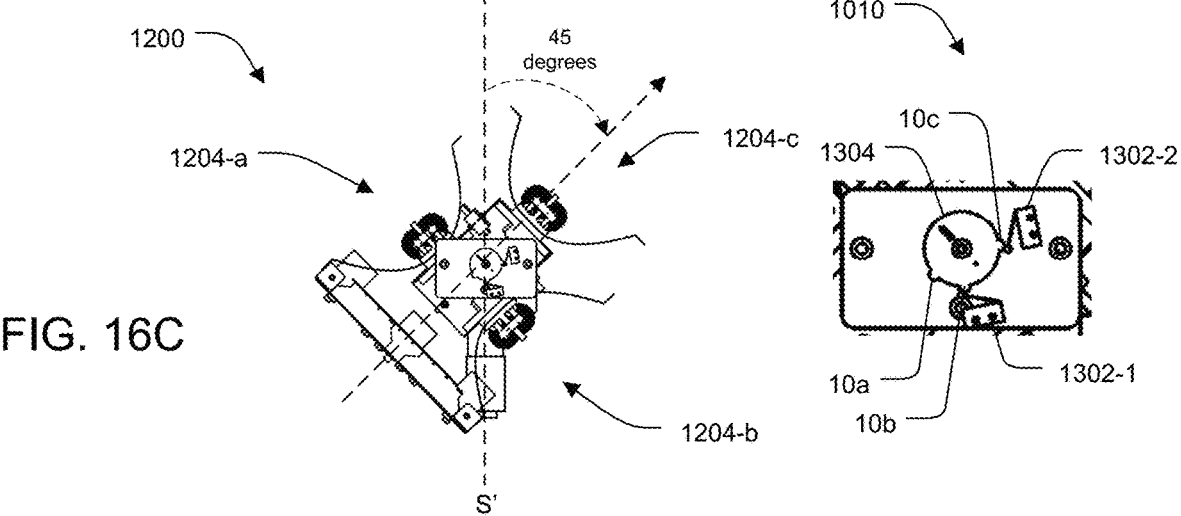

In a first embodiment, as illustrated in FIGS. 16A-16C, the projection head 110 may be implemented in the open configuration for operation. In the open configuration, the lamp assembly 1200 may be coupled to the rotation assembly without the lamp housing 1002 for operation. The rotation assembly may be operated to transition the lamp assembly 1200 between a stationary position and one or more rotary positions. In the stationary position (FIG. 16A), the lamp assembly 1200 may include the radiation units 1204 oriented away from each other and operating to project the UV light towards surfaces in different planes or directions relative to the mobile body 108 or the projection device 100. For example, in the stationary position, the first radiation unit 1204-a and the second radiation unit 1204-b may be oriented to project the UV light across the sagittal plane SS' in a first direction and a second direction respectively. The second direction may be opposite to the first direction. In some examples, the second direction may be parallel to the first direction. The first radiation unit 1204-a and the second radiation unit 1204-b may be located in the same plane with the third radiation unit 1204-c located therebetween. In the illustrated example, the third radiation unit 1204-c is positioned above the first radiation unit 1204-a and the second radiation unit 1204-b; however, other examples may include the third radiation unit 1204-c being positioned with one of the first radiation unit 1204-a and the second radiation unit 1204-b. The third radiation unit 1204-c may be oriented to project the UV light along a vertical axis in the sagittal plane SS' in a third plane in the stationary position. In some examples, the third direction may be orthogonal to at least one of the first direction and the second direction. Each of the radiation units 1204 may be arranged around the shaft 1012 defining an axis of rotation of the lamp assembly 1200, and the projection head 110. The axis of rotation may extend along the horizontal axis in the sagittal plane SS'.

The stationary position of the shaft 1012 and the lamp assembly 1200 may be sensed by the controller 302 based on a first engagement of a set of contact pins 10 with the contact sensors 1302 in the sensor block 1010. For instance, the sensor block 1010 may provide a first position signal based on pin 10a engaging with the first contact sensor 1302-1 while pin 10b and pin 10c being disengaged from the contact sensors 1302. The first position signal may indicate the stationary position of the lamp assembly 1200 to the controller 302. The lamp assembly 1200 may be rotated from the stationary position based on a rotation of the shaft 1012 in the rotation assembly. The shaft 1012 may be rotated in a preset or dynamically set direction by the controller 302 during the operational cycle. For example, the controller 302 may trigger the motor 1008-1 to rotate the shaft 1012 (via the bevel-gear arrangement 1008-2) either clockwise or anticlockwise. In one instance, the shaft 1012 may be rotated anticlockwise to transition the lamp assembly 1200 from the stationary position to a first rotary position.

As illustrated in FIG. 16B, in the first rotary position, the lamp assembly 1200 may rotate anticlockwise up to a first rotation angle across the sagittal plane SS'. In one example, the first rotation angle may be approximately 45 degrees relative to the sagittal plane SS'; however, other examples may include the first rotation angle up to approximately 90 degrees. Such anticlockwise rotation may orient the first radiation unit 1204-a and the second radiation unit 1204-b downwards and upwards respectively relative to the axis of rotation. In the downward orientation, the first radiation unit 1204-a may project the UV light towards surfaces located below the axis of rotation and along a first side of the sagittal plane SS'. In some instances, the surfaces below the axis of rotation may include the ground or a portion of path being traversed by the projection device 100. In the upward orientation, the second radiation unit 1204-b may project the UV light towards surfaces located above the axis of rotation and along a second side of the sagittal plane SS'. Simultaneously, the third radiation unit 1204-c may be oriented to project the UV light towards surfaces located above the axis of rotation and along the first side of the sagittal plane SS'.

The first rotary position of the lamp assembly 1200 may be sensed by the controller 302 based on a second engagement of a set of contact pins 10 with the contact sensors 1302 in the sensor block 1010. For instance, the sensor block 1010 may provide a second position signal based on pin 10b engaging with the second contact sensor 1302-2 while pin 10a and pin 10c being disengaged from the contact sensors 1302 due to the anticlockwise rotation of the shaft 1012. The second position signal may indicate the first rotary position of the lamp assembly 1200 to the controller 302. Similarly, in another instance, the shaft 1012 may be rotated clockwise to transition the lamp assembly 1200 to a second rotary position.

As illustrated in FIG. 16C, in the second rotary position, the lamp assembly 1200 may rotate clockwise up to a second rotation angle across the sagittal plane SS'. In one example, the second rotation angle may be approximately 45 degrees relative to the sagittal plane SS'; however, other examples may include the second rotation angle up to approximately 90 degrees. Such clockwise rotation may orient the first radiation unit 1204-a and the second radiation unit 1204-b upwards and downwards respectively relative to the axis of rotation. In the upward orientation, the first radiation unit 1204-a may project the UV light towards surfaces located above the axis of rotation and along the first side of the sagittal plane SS'. Simultaneously, the third radiation unit 1204-c may be oriented to project the UV light towards surfaces located above the axis of rotation and along the second side of the sagittal plane SS'. On the other hand, in the downward orientation, the second radiation unit 1204-b may project the UV light towards surfaces located below the axis of rotation and along the second side of the sagittal plane SS'. The second rotary position of the lamp assembly 1200 may be sensed by the controller 302 based on a third engagement of a set of contact pins 10 with the contact sensors 1302 in the sensor block 1010. For instance, the sensor block 1010 may provide a third position signal based on pin 10*b* engaging with the first contact sensor 1302-1 and pin 10*c* engaging with the second contact sensor 1302-2 while pin 10*a* being disengaged from the contact sensors 1302 due to the clockwise rotation of the shaft 1012. The third position signal may indicate the second rotary position of the lamp assembly 1200 to the controller 302.

In a second embodiment, as illustrated in FIGS. 17A-17C, the projection head 110 may be implemented in the closed configuration. In the closed configuration, the lamp assembly 1200 may be located within the lamp housing 1002 coupled to the rotation assembly for operation. The rotation assembly may be operated to transition the lamp housing 1002 (or the projection head 110) between the stationary position and one or more tilt positions, which may be synchronized with the first and second rotary positions, discussed above. Each of the tilt positions may be determined by the controller 302 in communication with the sensor block 1010 as discussed above.

In the stationary position (FIG. 17A), the lamp housing 1002 (or the projection head 110) may be located within the exterior planes of the autonomous vehicle 112. The lamp housing 1002 (or the projection head 110) may include the first lateral plate 1004-1 positioned proximate to the first radiation unit 1204-*a* oriented towards the first lateral side 102-1 of the mobile body 108. Opposite to the first lateral plate 1004-1, the lamp housing 1002 (or the projection head 110) may include the second lateral plate 1004-2 positioned proximate to the second radiation unit 1204-*b* oriented towards the second lateral side 102-2 of the mobile body 108. The first lateral plate 1004-1 may include the first window 1006-1 arranged parallel to the second window 1006-2 of the second lateral plate 1004-1. Each of the first window 1006-1 and the second window 1006-2 may be parallel to the sagittal plane SS' passing therebetween. The first window 1006-1 and the second window 1006-2 may be located in the same horizontal plane with the top plate 1002-3 of the lamp housing 1002 located therebetween. The top plate 1002-3 may be positioned above the lateral plates 1004 of the lamp housing 1002. The top plate 1002-3 may include the third window 1006-3 proximate to the third radiation unit 1204-*c*. The third window 1006-3 may be arranged perpendicular to a vertical axis in the sagittal plane SS'. The windows 1006 may enable the radiation units 1204 to emit the UV light exterior to the lamp housing 1002 (or the projection head 110). For example, the first radiation unit 1204-*a* may project the UV light through the first window 1006-1 towards surfaces proximate to the first lateral side 102-1 of the mobile body 108. The second radiation unit 1204-*b* may project the UV light through the second window 1006-2 towards surfaces proximate to the second lateral side 102-2 of the mobile body 108. The third radiation unit 1204-*c* may project the UV light through the third window 1006-3 towards surfaces above the lamp housing 1002 (or the projection head 110), and the mobile body 108. The windows 1006 may be arranged around the shaft 1012 passing through the lamp housing 1002. The stationary position of the shaft 1012 and the lamp housing 1002 (or the projection head 110) may be sensed by the controller 302 based on the first position signal from the sensor block 1010 as discussed above. The shaft 1012 may be rotated by the controller 302 to tilt the lamp housing 1002 (or the projection head 110) across the sagittal plane SS'. The lamp housing 1002 (or the projection head 110) may tilt with the lamp assembly 1200 based on a rotation of the shaft 1012. In one example, the shaft 1012 may be rotated anticlockwise to transition the lamp housing 1002 (or the projection head 110) from the stationary position to a first tilt position.

As illustrated in FIG. 17B, in the first tilt position, the lamp housing 1002 (or the projection head 110) may tilt up to a predefined tilt angle towards the first lateral side 102-1 of the mobile body 108. In one example, the tilt angle may be approximately 45 degrees relative to the sagittal plane SS'; however, other examples may include the tilt angle up to approximately 90 degrees. Such tilt may orient the first lateral plate 1004-1 (and the first window 1006-1) downwards as well as the second lateral plate 1004-2 (and the second window 1006-2) upwards relative to the axis of rotation defined by the shaft 1012. In the downward orientation, the first radiation unit 1204-*a* may project the UV light through the first window 1006-1 towards surfaces located below the axis of rotation and proximate to the first lateral side 102-1 of the mobile body 108. In some instances, the surfaces below the axis of rotation may include the ground or a portion of path being traversed by the projection device 100. In the upward orientation, the second radiation unit 1204-*b* may project the UV light through the second window 1006-2 towards surfaces located above the axis of rotation and proximate to the second lateral side 102-2 of the mobile body 108. Simultaneously, the third radiation unit 1204-*c* may be oriented to project the UV light through the third window 1006-3 in the top plate 1002-3 towards surfaces located above the axis of rotation and proximate the first lateral side 102-1 of the mobile body 108. Since the lamp housing 1002 tilts with the lamp assembly 1200, the first tilt position of the lamp housing 1002 (or the projection head 110) may be sensed by the controller 302 based on the second position signal from the sensor block 1010 as discussed above.

Similarly, in another example, the shaft 1012 may be rotated clockwise to transition the lamp housing 1002 (or the projection head 110) to a second tilt position. As illustrated in FIG. 17C, in the second tilt position, the lamp housing 1002 (or the projection head 110) may tilt up to a predefined tilt angle towards the second lateral side 102-2 of the mobile body 108. In one example, the tilt angle may be approximately 45 degrees relative to the sagittal plane SS'; however, other examples may include the tilt angle up to approximately 90 degrees. Such tilt may orient the first lateral plate 1004-1 (and the first window 1006-1) upwards and the second lateral plate 1004-2 (and the second window 1006-2) downwards relative to the axis of rotation defined by the shaft 1012. In the upward orientation, the first radiation unit 1204-*a* may project the UV light through the first window 1006-1 towards surfaces located above the axis of rotation and proximate to the first lateral side 102-1 of the mobile body 108. In the downward orientation, the second radiation unit 1204-*b* may project the UV light through the second window 1006-2 towards surfaces located below the axis of rotation and proximate to the second lateral side 102-2 of the mobile body 108. In some instances, the surfaces below the axis of rotation may include the ground or a portion of path being traversed by the projection device 100. Simultaneously, the third radiation unit 1204-*c* may be oriented to project the UV light through the third window 1006-3 in the top plate 1002-3 towards surfaces located above the axis of rotation and proximate the second lateral side 102-2 of the mobile body 108. Since the lamp housing 1002 tilts with the lamp assembly 1200, the second tilt position of the lamp housing 1002 (or the projection head 110) may be sensed by the controller 302 based on the third position signal from the sensor block 1010 as discussed above.

Hence, the clockwise and anticlockwise rotations of the shaft 1012 may tilt (or rotate) the projection head 110 up to the predefined tilt (or rotation) angle in opposite directions across the sagittal plane SS'. The tilt/rotation angle may be set based on a minimum distance up to which the projection head 110 may be intended to project the UV light downwardly without casting a shadow of the projection device 100 on a target surface. Such minimum distance may depend on a height of the projection head 110 from the ground. In one instance, the projection head 110 may be positioned at a height of at least 38 inches (or 96 centimeters) from the ground for the tilt/rotation angle of 45 degrees; however, other instances may include such tilt angle being increased to an angle greater than 45 degrees relative to a vertical axis of the sagittal plane SS' based on the height of the projection head 110 being greater than 38 inches, and vice versa.

In one embodiment, the projection device 100 including the projection head 110 may be employed for targeted disinfection of surfaces, e.g., within an aircraft 1800 (FIGS. 18A-18C); however, other embodiments may include the projection device 100 or the projection head 110 being employed for any other task or operation including those mentioned above.

During operation, the controller 302 may operate the projection device 100 in a manual mode or an automated mode (hereinafter collectively referred to as device modes). In the automated mode, the controller 302 may drive (i) the mobility device, such as the autonomous vehicle 112, autonomously or via a remote device for moving or orienting the projection device 100 proximate to a target surface and/or along a path such as an aircraft aisle. The automated mode, in some examples, may also include the controller 302 driving the projection head 110 to automatically project the germicide such as UV light based on, at least one of, (a) a speed or direction of movement of the autonomous vehicle 112, (b) number of rotations of the projection head 110 per unit time (e.g., second, minute, etc.) or per operational cycle such as the disinfection cycle, (c) speed or direction of rotations of the projection head 110, (d) object aspects such as those mentioned above including proximity to a target surface or an intended path, and/or (e) a preset duration, the pulse frequency, or the toggling rate associated with the projection head 110 within an operational cycle such as a disinfection cycle. In the manual mode, the controller 302 may enable an operator to manually (a) move or steer the mobility device (e.g., autonomous vehicle 112) or the projection device 100 and (b) remotely control a projection of the germicide such as UV light from the projection head 110.

In another example, the controller 302 may additionally operate the projection head 110 in one of a rotary mode and a stationary mode (hereinafter collectively referred to as projection modes). In the stationary mode, the projection head 110 may be kept stationary within the exterior planes. In the rotary mode, the controller 302 may drive the projection head 110 to tilt (or rotate) for changing the planes or directions in which the germicide such as UV light may be projected therefrom. In a further example, the controller 302 may also operate in a peripheral mode to enable operation of a peripheral component such as the handheld projection device 802 upon being operationally connected to the projection device 100. Each of the device modes, the projection modes, and the peripheral mode (collectively referred to as the operational modes) may be implementable to operate independently, or in tandem with each other, in any suitable combination or order. However, some examples may include a particular operational mode being operable mutually exclusive to one or more of the remaining operational modes. For instance, the controller 302 may implement the peripheral mode based on the projection modes and the automated mode being deactivated. In some instances, the controller 302 may automatically deactivate the automated mode and the projection modes based on the peripheral mode being selected. These operational modes may be selected by a user using any of the suitable input devices known in the art. For example, the user may login on an input device such as an interactive display screen of a mobile computing device operating in communication with the controller 302 of the projection device 100 to select one or more of these modes for operation.

Figure 18A:
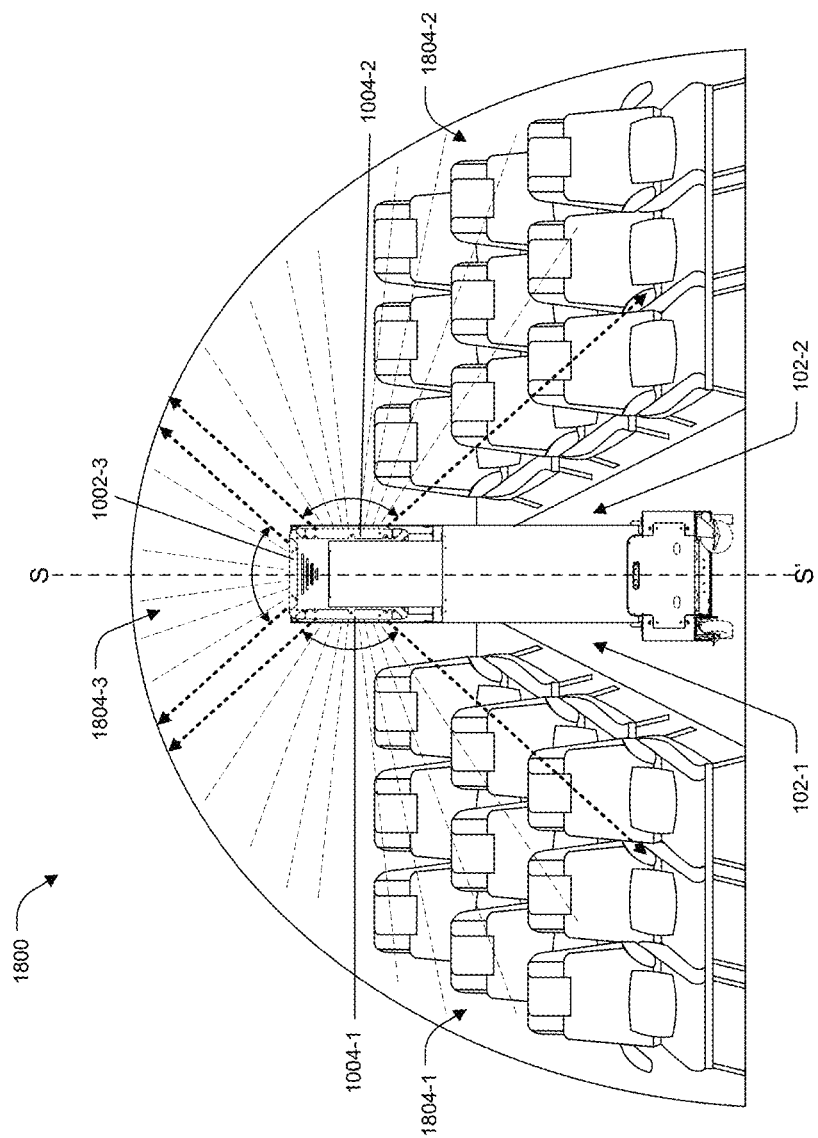
FIGS. 18A-18C illustrate an exemplary scenario to implement the projection device of FIG. 1A for surface disinfection, according to an embodiment of the present disclosure.
Figure 18B:
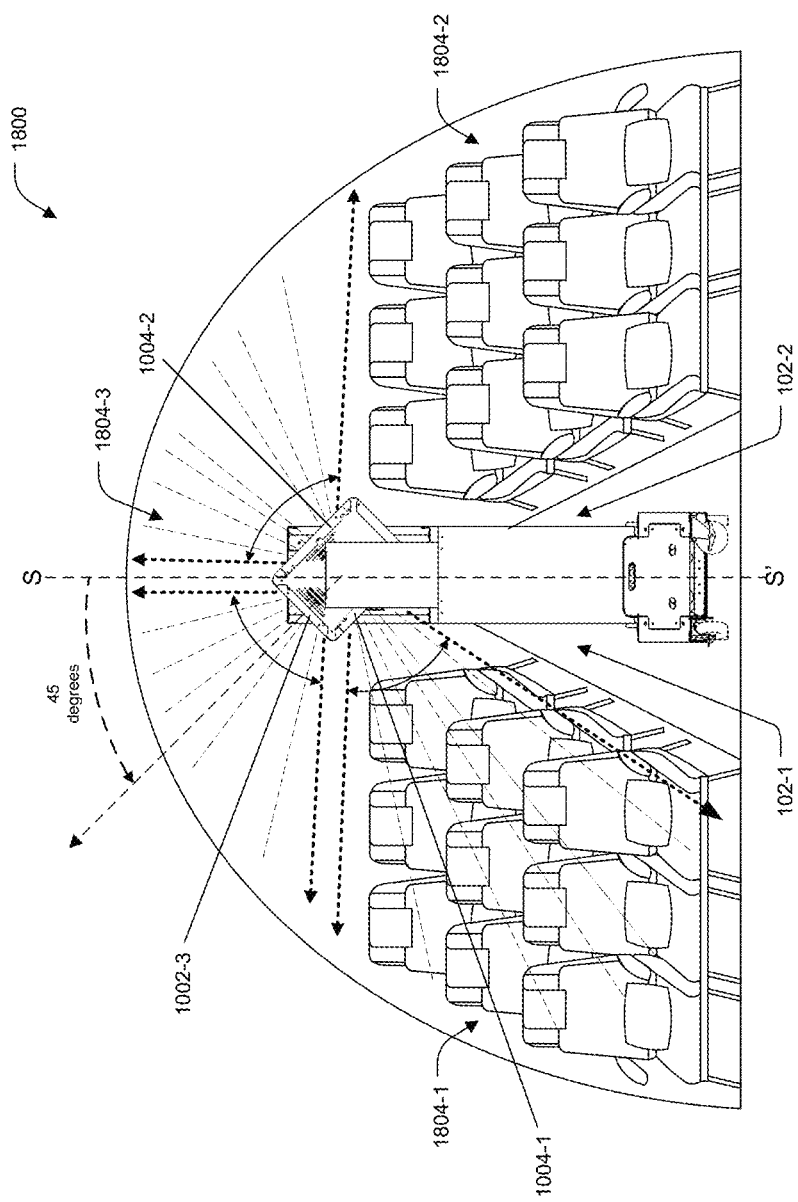
Figure 18C:
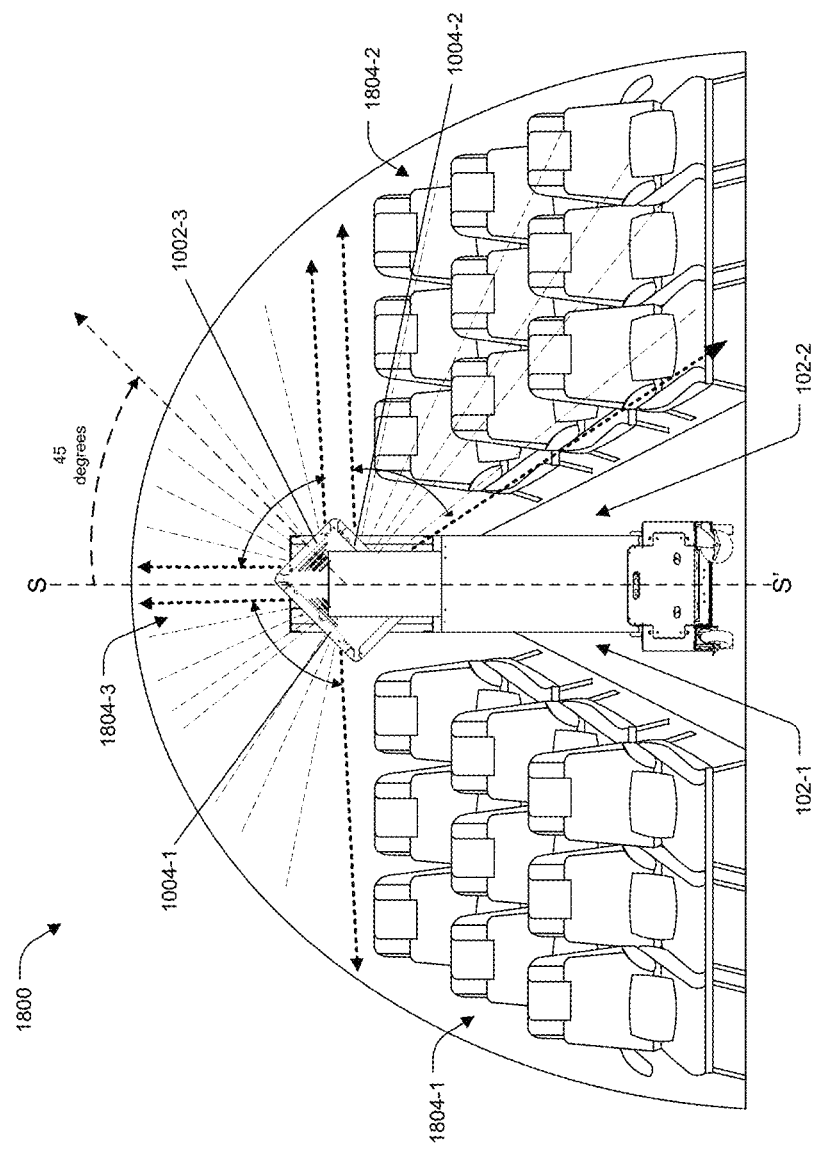

As illustrated in FIGS. 18A-18C, the projection device 100 may be driven along a path such as an aircraft aisle to disinfect surfaces (e.g., seats, overhead luggage compartments, etc.) located above and proximate to the lateral sides 102. The projection device 100 may be operated by the controller 302 to traverse the path autonomously based on the automated mode being selected, or driven manually based upon the manual mode being selected. While traversing the path, the projection device 100 may be operated to project UV light from the projection head 110 towards the surfaces. As illustrated, the aircraft 1800 may include a first set of surfaces 1804-1 proximate to the first lateral side 102-1, a second set of surfaces 1804-2 proximate to the second lateral side 102-2, and a third set of surfaces 1804-3 above the projection head 110, or the projection device 100. Each of the first set of surfaces 1804-1, the second set of surfaces 1804-2, and the third set of surfaces 1804-3 (hereinafter collectively referred to as proximate surfaces 1804) may be located in an arch extending across from the sagittal plane SS' of the projection device 100. The projection device 100 may be set to operate in one of the stationary mode, the rotary mode, and the peripheral mode for disinfecting the proximate surfaces 1804.

Stationary Mode

When the stationary mode is selected, the controller 302 may deactivate the rotary mode and the peripheral mode for the projection device 100. The controller 302 may implement the stationary mode with any of the selected device modes including the automated mode and the manual mode. During the stationary mode, in one embodiment (FIG. 18A), the controller 302 may set up the projection head 110 (including the lamp assembly 1200) in the stationary position while projecting the germicide such as UV light therefrom towards the proximate surfaces 1804. The projection head 110 may include the lamp housing 1002 located within the exterior planes and the sagittal plane SS' passing therethrough in the stationary position. The lamp housing 1002 may be operable to rotate about a horizontal axis in the sagittal plane SS' and surround the lamp assembly 1200 of the projection head 110. Further in the stationary position, the lamp housing 1002 may include the lateral plates 1004 and the top plate 1002-3 positioned orthogonal thereto. The lateral plates 1004 may be arranged parallel to the sagittal plane SS' and the top plate 1002-3 may be arranged perpendicular to the sagittal plane SS'. In the stationary mode, the controller 302 may trigger the projection head 110 (or the lamp assembly 1200) to project the UV light through respective windows 1006 in the lateral plates 1004 and the top plate 1002-3 towards the ambient proximate surfaces 1804 (e.g., seats, walls, ceiling, etc.) located exterior to the projection device 100. In some instances, the controller 302 may trigger the projection head 110 (or the lamp assembly 1200) to project the UV light towards the proximate surfaces 1804 alternately in any predefined order during the disinfection cycle. Other instances may include the controller 302 triggering the projection head 110 (or the lamp assembly 1200) to project the UV light towards only one or a set of any two of the proximate surfaces 1804 for disinfection. The controller 302 may sense the stationary position of the projection head 110 (or the lamp housing 1002) based on the first position signal from the sensor block 1010, as discussed above.

Rotary Mode

When the rotary mode is selected, the controller 302 may deactivate the stationary mode and the peripheral mode for the projection device 100. The controller 302 may implement the rotary mode with any of the device modes including the automated mode and the manual mode. During the rotary mode, the controller 302 may drive the rotation assembly to rotate the projection head 110 (including the lamp assembly 1200) in at least one direction across the sagittal plane SS'. The projection head 110 may include the lamp housing 1002 rotating with the lamp assembly 1200 based on the shaft 1012 in the rotation assembly being driven by the controller 302, as discussed above. In one example, the controller 302 may alternately rotate the shaft 1012 clockwise and anticlockwise within the disinfection cycle. The shaft 1012 may be rotated about a horizontal axis in the sagittal plane SS' to rotate the projection head 110. During the anticlockwise rotation (FIG. 18B), the projection head 110 may be rotated to tilt the lamp housing 1002 across the sagittal plane SS' up to a predefined tilt angle (e.g., 45 degrees) relative to the sagittal plane SS'. Such anticlockwise tilt may drive the projection head 110 to the first rotary/tilt position from the stationary position.

In the first rotary/tilt position, the projection head 110 including the lamp assembly 1200 may rotate (or tilt) with the lamp housing 1002 towards the first lateral side 102-1 of the mobile body 108, or the projection device 100, across the sagittal plane SS'. The lamp housing 1002 may include the first lateral plate 1004-1 orienting downwards and the second lateral plate 1004-2 orienting upwards in this position. In the downward orientation, the projection head 110 (including the lamp assembly 1200) may project the UV light through the window 1006-1 in the first lateral plate 1004-1 for disinfecting portions of the first set of surfaces 1804-1, where these portions may be located below the axis of rotation defined by the longitudinal axis of the shaft 1012. In some instances, these portions below the axis of rotation may include the ground such as a part of the aircraft aisle being traversed by the projection device 100. The downward orientation may assist to disinfect adjacent surfaces (e.g., seat handles) that may be outside a trajectory of UV light projected in the stationary position of the projection head 110 due to the adjacent surface being relatively closer (e.g., less than one meter) to the first lateral side 102-1 of the mobile body 108.

In the upward orientation, the projection head 110 (including the lamp assembly 1200) may project the UV light through the window 1006-2 in the second lateral plate 1004-2 for disinfecting portions of the second set of surfaces 1804-2 and the third set of surfaces 1804-3, where these portions may be located above the axis of rotation of the projection head 110. In some instances, simultaneously, the projection head 110 (including the lamp assembly 1200) may be operated by the controller 302 to project the UV light through the window 1006-3 in the top plate 1002-3 for disinfecting portions of the first set of surfaces 1804-1 and the third set of surfaces 1804-3, where these portions may be located above the axis of rotation of the projection head 110.

The controller 302 may determine the first rotary/tilt position of the projection head 110 (or the lamp housing 1002) based on the second position signal from the sensor block 1010, as discussed above. In response to determining the first rotary/tilt position, the controller 302 may rotate the shaft 1012 in the reverse direction (such as clockwise direction) and return the projection head 110 (or the lamp housing 1002) to the stationary position. However, some instances may include the controller 302 operating the shaft 1012 to selectively maintain the projection head 110 (or the lamp housing 1002) at the first rotary/tilt position for a predefined duration within the disinfection cycle. Upon returning to the stationary position, the sensor block 1010 may assist to detect such position of the projection head 110 (or the lamp housing 1002) and trigger the controller 302 to rotate the shaft 1012 in the clockwise direction within the same disinfection cycle or a predefined period thereafter.

During the clockwise rotation (FIG. 18C), the projection head 110 may be rotated to tilt the lamp housing 1002 across the sagittal plane SS' up to a predefined tilt angle (e.g., 45 degrees) relative to the sagittal plane SS'. Such clockwise tilt may drive the projection head 110 to the second rotary/tilt position from the stationary position. In the second rotary/tilt position, the projection head 110 including the lamp assembly 1200 may rotate (or tilt) with the lamp housing 1002 towards the second lateral side 102-2 of the mobile body 108, or the projection device 100, across the sagittal plane SS'. The lamp housing 1002 may include the second lateral plate 1004-2 orienting downwards and the first lateral plate 1004-1 orienting upwards in this position. In the downward orientation, the projection head 110 (including the lamp assembly 1200) may project the UV light through the window 1006-2 in the second lateral plate 1004-2 for disinfecting portions of the second set of surfaces 1804-2, where these portions may be located below the axis of rotation of the projection head 110. In some instances, these portions below the axis of rotation may include the ground such as a part of the aircraft aisle being traversed by the projection device 100. The downward orientation may assist to disinfect adjacent surfaces (e.g., seat handles) that may be outside a trajectory of UV light projected in the stationary position of the projection head 110 due to the adjacent surface being relatively closer (e.g., less than one meter) to the second lateral side 102-2 of the mobile body 108.

In the upward orientation, the projection head 110 (including the lamp assembly 1200) may project the UV light through the window 1006-1 in the first lateral plate 1004-2 for disinfecting portions of the first set of surfaces 1804-1 and the third set of surfaces 1804-3, where these portions may be located above the axis of rotation of the projection head 110. In some instances, simultaneously, the projection head 110 (including the lamp assembly 1200) may be operated by the controller 302 to project the UV light through the window 1006-3 in the top plate 1002-3 for disinfecting portions of the first set of surfaces 1804-1 and the third set of surfaces 1804-3, where these portions may be located above the axis of rotation of the projection head 110.

The controller 302 may determine the second rotary/tilt position of the projection head 110 (or the lamp housing 1002) based on the third position signal from the sensor block 1010, as discussed above. In response to determining the second rotary/tilt position, the controller 302 may rotate the shaft 1012 in the reverse direction (such as anticlockwise direction) and return the projection head 110 (or the lamp housing 1002) to the stationary position. However, some instances may include the controller 302 operating the shaft 1012 to selectively maintain the projection head 110 (or the lamp housing 1002) at the second rotary/tilt position for a predefined duration within the disinfection cycle. Upon returning to the stationary position, the controller 302 may determine such position of the projection head 110 (or the lamp housing 1002) and continue rotating the shaft 1012 between the anticlockwise direction and the clockwise direction within the disinfection cycle. Hence, the projection head 110 operates in the stationary and the rotary/tilt positions to project the UV light for disinfecting surfaces, such as the proximate surfaces 1804, located above and lateral to the device 100 while limiting UV dispersion towards the front side 104 and the rear side 106 of the mobile body 108, or the projection device 100. Other examples may include the controller 302 alternately rotating the shaft 1012 for rotating/tilting the projection head 110 between the stationary position and one of the rotary/tilt positions in the rotary mode.

Peripheral Mode

In a further embodiment, the operator may select the peripheral mode to operate a peripheral component such as the handheld projection device 802 (e.g., handheld UV device) attached to the auxiliary frame 602 of the projection device 100. Some examples may include the controller 302 deactivating the projection modes and the automated mode of the projection device 100 upon selection of the peripheral mode. In the peripheral mode, the auxiliary frame 602 may couple the attached handheld projection device 802 to the control system. The handheld projection device 802 may be powered (via the battery) and/or controlled by the controller 302 for manually disinfecting surfaces that may be outside the trajectories of UV light projected by the projection head 110 in the stationary position and the rotary/tilt positions.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiments, methods, and examples, but by all embodiments and methods within the scope and spirit of the invention(s).

We claim:

1. An apparatus for projecting UV light towards surfaces across a path, the apparatus comprising:
    a mobile body including opposing lateral sides and a sagittal plane passing therebetween; and
    a projection head rotatably mounted to the mobile body, the projection head operating to project UV light directionally towards surfaces located above and proximate to the opposing lateral sides, wherein the projection head is adapted to rotate about a horizontal axis in the sagittal plane while the UV light is being projected towards the surfaces, wherein the projection head includes a set of radiation units for projecting the UV light, wherein the set includes a first radiation unit and a second radiation unit respectively oriented towards each of the opposing lateral sides and wherein each of the radiation units in the set of radiation units is fixed relative to the other radiation units in the set of radiation units.

2. The apparatus of claim 1, wherein the projection head is further adapted to tilt up to a predefined tilt angle towards at least one of the opposing lateral sides across the sagittal plane.

3. The apparatus of claim 2, wherein the tilt angle is 45 degrees relative to the sagittal plane.

4. The apparatus of claim 1, further comprising a housing proximate to the projection head, wherein the housing includes a portion at least in-part permeable to the UV light.

5. The apparatus of claim 4, wherein the housing is supported by the opposing lateral sides.

6. The apparatus of claim 1, wherein the set further includes a third radiation unit located between the first radiation unit and the second radiation unit, wherein the third radiation unit is oriented to project the UV light towards a surface above the horizontal axis.

7. The apparatus of claim 6, wherein the third radiation unit is oriented to project the UV light in a first direction orthogonal to a second direction of projection associated with at least one of the first radiation unit and the second orientation unit.

8. The apparatus of claim 1, wherein the radiation units are oriented away from each other.

9. The apparatus of claim 1, wherein the projection head is located at a height of at least 38 inches (or 96 centimeters) from the ground.

10. The apparatus of claim 1, wherein the mobile body further includes a tray pivotably attached thereto, the tray being pivotable to transition between a closed position and an open position, wherein the tray is parallel to a vertical axis in the closed position and non-parallel to the vertical axis in the open position.

11. The apparatus of claim 10, wherein the tray is pivotable to at least partially extend outward from one of the opposing lateral sides in the open position.

12. The apparatus of claim 10, wherein the tray includes a support surface for carrying operational components of the apparatus, wherein the support surface is parallel to the vertical axis in the closed position.

13. The apparatus of claim 1, wherein the mobile body is adapted to move the apparatus autonomously while the projection head rotates about the horizontal axis.

14. The apparatus of claim 1, wherein the projection head operates to project the UV light towards the surfaces alternately within an operational cycle.

15. The apparatus of claim 1, further comprising a plurality of windows providing for the projection head to directionally project the UV light.

16. The apparatus of claim 1, wherein the mobile body includes a camera.

17. The apparatus of claim 1, wherein at least one of the mobile body and the projection head are operable via a remote device.

18. The apparatus of claim 1, further comprising a handheld device operably connected to the apparatus.

19. The apparatus of claim 1, wherein the projection head is implementable on a handheld device.

* * * * *